United States Patent [19]

Schultz

[11] Patent Number: 5,162,218

[45] Date of Patent: Nov. 10, 1992

[54] CONJUGATED POLYPEPTIDES AND METHODS FOR THEIR PREPARATION

[75] Inventor: Peter Schultz, Oakland, Calif.

[73] Assignee: The Regents of the University of California, Oakland, Calif.

[21] Appl. No.: 713,623

[22] Filed: Jun. 10, 1991

Related U.S. Application Data

[63] Continuation of Ser. No. 273,786, Nov. 18, 1988, abandoned.

[51] Int. Cl.$^5$ .................... C12N 11/06; C07K 15/28; C07K 15/14; C07K 15/18; C07K 17/06
[52] U.S. Cl. ............................ 435/188; 435/188.5; 530/391.1; 530/391.3; 530/391.5; 530/391.7; 530/391.9; 530/345; 530/350; 530/351; 530/395; 530/396; 530/397; 530/399; 530/404; 530/405; 530/406; 530/408; 530/409; 530/410; 424/85.91; 436/537; 436/547; 436/501; 436/544; 436/546
[58] Field of Search ............... 530/389, 390, 391, 408, 530/391.1, 391.3, 391.5, 391.7, 391.9, 350, 351, 395, 345, 358, 395, 396, 397, 399, 404, 405, 406, 409, 410; 424/85.91; 435/188, 188.5, 964; 436/537, 547, 501, 544, 546

[56] References Cited

U.S. PATENT DOCUMENTS

| | | | |
|---|---|---|---|
| 3,817,752 | 6/1974 | Laridon et al. | 430/335 |
| 4,059,685 | 11/1977 | Johnson | 424/28 |
| 4,340,535 | 7/1982 | Voisin et al. | 530/388 |
| 4,368,149 | 1/1983 | Masuho et al. | 530/388 |
| 4,489,710 | 12/1984 | Spitler | 128/898 |
| 4,671,958 | 6/1987 | Rodwell et al. | 424/85.91 |
| 4,722,906 | 2/1988 | Guire | 436/501 |
| 4,792,446 | 12/1988 | Kim et al. | 425/85.8 |
| 4,888,281 | 12/1989 | Schochetman et al. | 435/72 |
| 4,900,674 | 2/1990 | Benkovic et al. | 435/232 |

FOREIGN PATENT DOCUMENTS

| | | |
|---|---|---|
| 0187658 | 7/1986 | European Pat. Off. ......... 424/85.91 |
| WO89/01782 | 3/1989 | PCT Int'l Appl. |
| WO89/01784 | 3/1989 | PCT Int'l Appl. |

OTHER PUBLICATIONS

Blair et al (1983) J. Immunol. Methods 59:129–143.
Breslow (1982) Science 218:532–537.
Haimovich et al (1972) Biochemistry 11(13) 2389–2398.
Webster et al. (1988) Int. J. Cancer (suppl. 3):13–16.
Baum (1987) Apr. 6th issue of C&EN pp. 30–33.
Pollack et al (1989) J. Am. Chem. Soc. 111:5961–5962.
Pollack et al (1989) Science 242:1038–1040.
Pollack et al (1989) J. Am. Chem. Soc. 111:1929–1931.
Jones et al. (1973) Eur. J. Biochem. 34:28–40.
(List continued on next page.)

*Primary Examiner*—Christine M. Nucker
*Assistant Examiner*—Kay K. Kim
*Attorney, Agent, or Firm*—Townsend and Townsend

[57] ABSTRACT

Polypeptide compositions are provided having a binding site specific for a particular target ligand and further having an active functionality proximate the binding site. The active functionality may be a reporter molecule, in which case the polypeptide compositions are useful in performing assays for the target ligand. Alternatively, the active functionality may be a chemotherapeutic agent, in which case the polypeptide compositions are useful for therapeutic treatment of various diseased states. A novel method for preparing such polypeptides having active functionalities proximate their binding site comprises combining the polypeptide specific for the target ligand with an affinity label including ligand having a reactive group attached thereto. The reactive group is then covalently attached to an amino acid side chain proximate the binding site and cleaved from the substrate. The substrate is eluted, leaving a moiety of the reactive group covalently attached to the polypeptide. The active funtionality may then be attached to the moiety.

21 Claims, 4 Drawing Sheets

OTHER PUBLICATIONS

Raso and Stollar (1975) Biochemistry 14:584–591.
Kohen et al. (1980) FEBS Lett. 111:427–431.
Goetzl and Metzger (1970) Biochemistry 9:1267–1278.
Givol et al. (1971) Biochemistry 10:3461–3466.
Wilkinson et al. (1984) Nature 307:187–188.
Craik et al. (1985) Science 228:291–297.
Schultz et al. (1985) Biochemistry 24:6840–6848.
Dalbadie-McFarland (1982) Proc. Natl. Acad. Sci. USA 79:6409–6413.
Sigal et al. (1984) J. Biol. Chem. 259:5327–5332.
Kaiser et al. (1984) Science 226:505–511.
Corey et al. (1987) Science 238:1401–1403.
Polgar and Bender (1966) J. Am. Chem. Soc. 88:3153–3154.
Neet and Koshland (1966) Proc. Natl. Acad. Sci. USA 56:1606–1611.

FIG_1
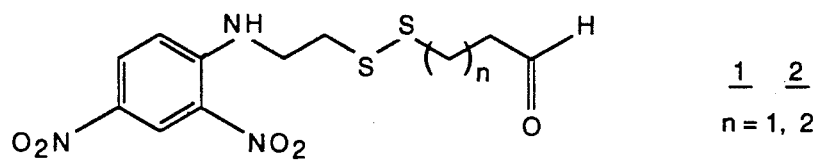
1  2
n = 1, 2
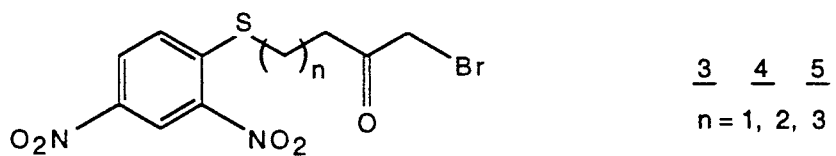
3  4  5
n = 1, 2, 3
FIG_3
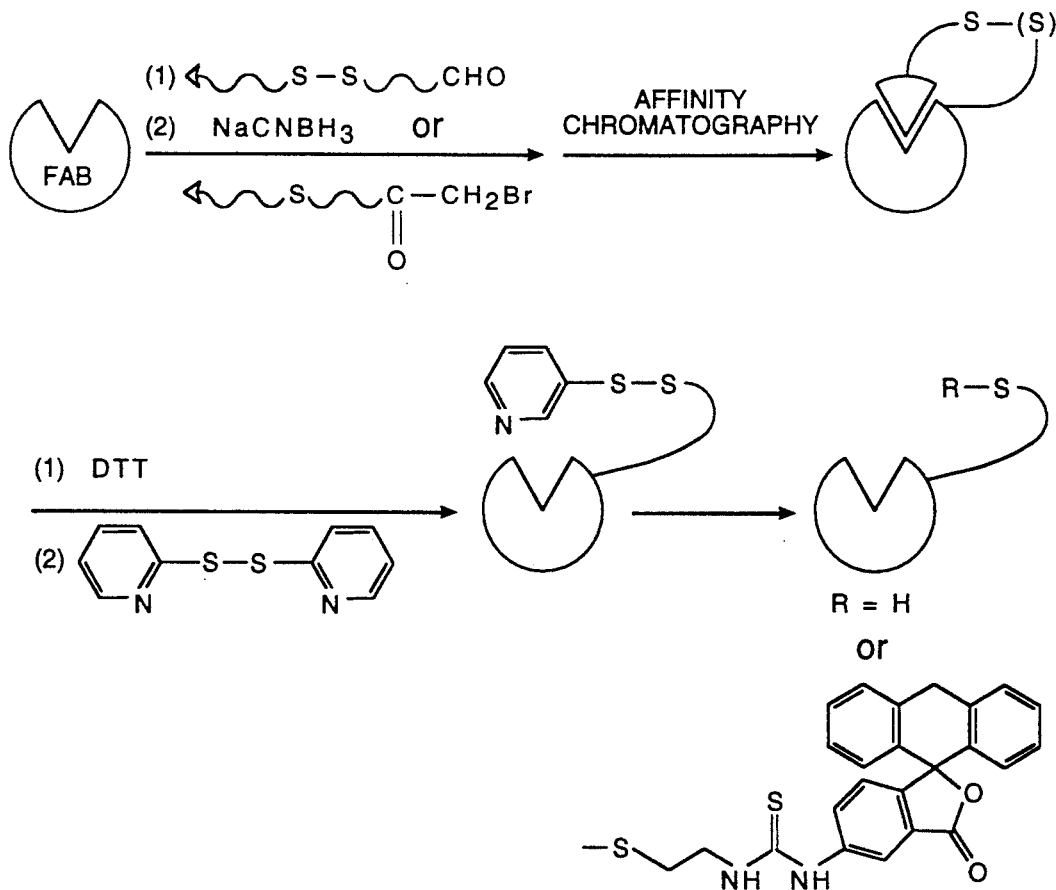

FIG_4
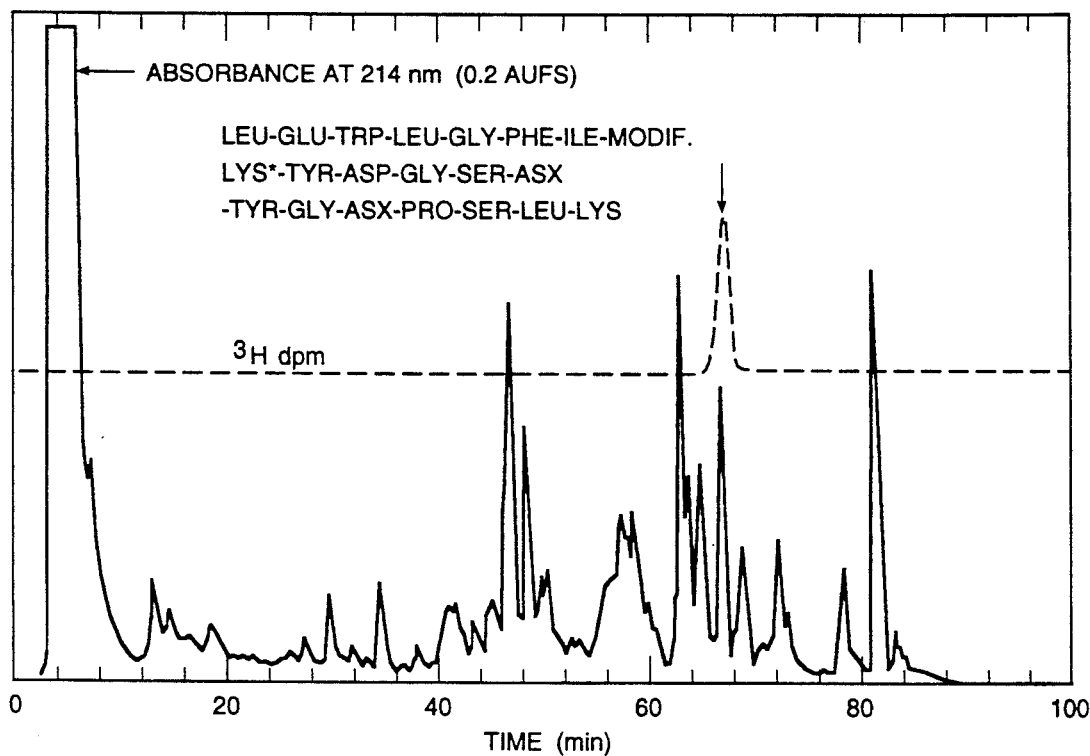
ABSORBANCE AT 214 nm (0.2 AUFS)
LEU-GLU-TRP-LEU-GLY-PHE-ILE-MODIF.
LYS*-TYR-ASP-GLY-SER-ASX
-TYR-GLY-ASX-PRO-SER-LEU-LYS
$^3$H dpm
TIME (min)
FIG_5
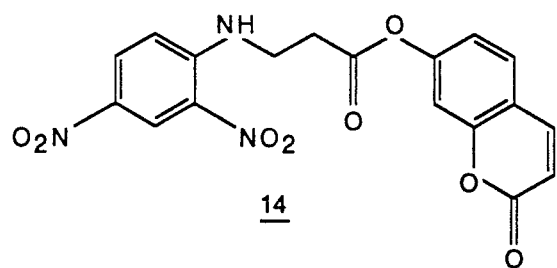
14
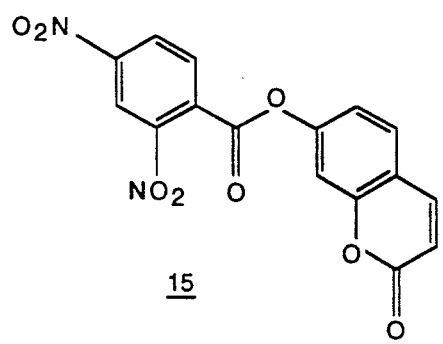
15

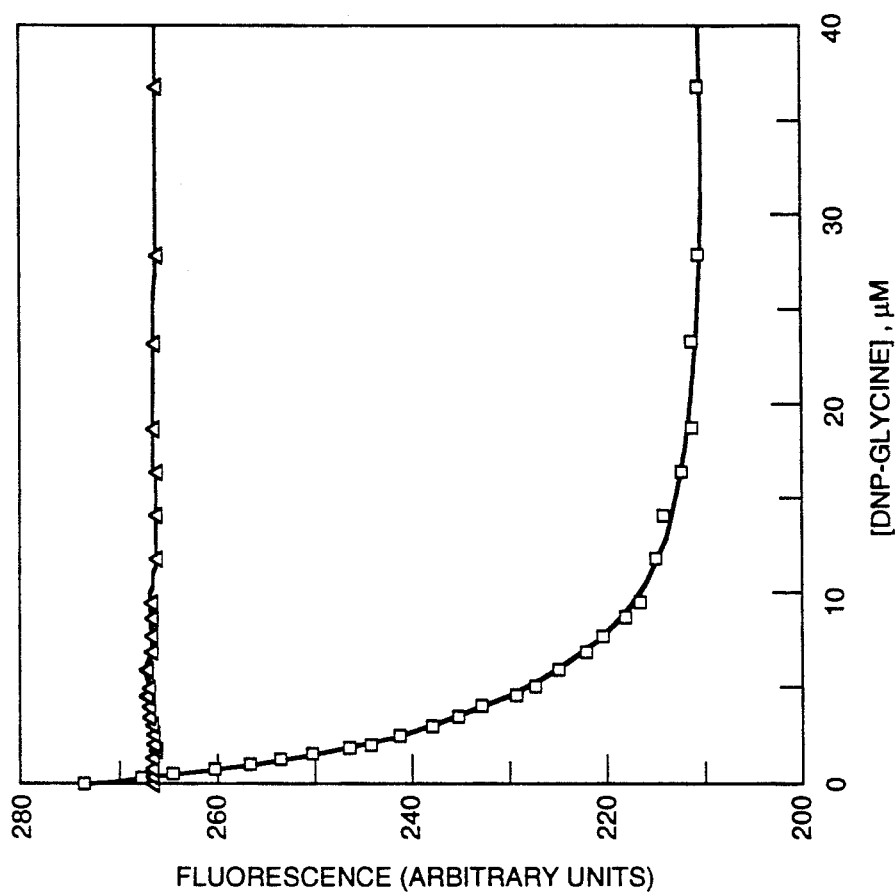
FIG_7
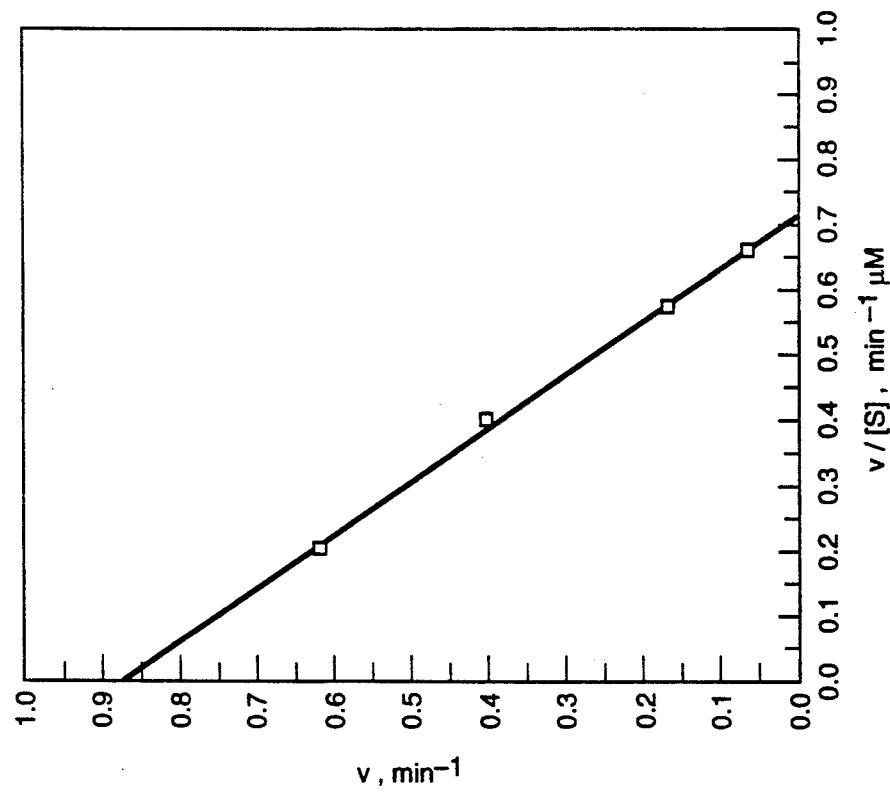
FIG_6

CONJUGATED POLYPEPTIDES AND METHODS FOR THEIR PREPARATION

This invention was made with Government support under Grant Contract No. AI-24695, awarded by the Department of Health and Human Services, and Under Grant Contract No. N 00014-87-K-0256, awarded by the Office of Naval Research. The Government has certain rights in this invention.

This is a continuation of application Ser. No. 07/273,786, filed Nov. 18, 1988, now abandoned.

Application Ser. No. 07/273,455, filed on the same date as the present application and naming Peter Schultz as the sole inventor, contains related subject matter. The entire disclosure of this related application is incorporated herein by reference.

BACKGROUND OF THE INVENTION

1. Field of the Invention

The present invention relates generally to polypeptide compositions having active functionalities covalently attached proximate a binding site. More particularly, the invention relates to polypeptides wherein the active functionality is a reporter molecule or a chemotherapeutic agent, and to methods for the preparation of such polypeptides.

Numerous biological proteins are capable of specific attachment to other biological molecules as a result of intermolecular binding forces, including electrostatic bonds, hydrogen bonds, and van der Waals bonds. Such bonding occurs at a site on the protein generally referred to as a binding site, and binding occurs only with target ligands having a specific molecular geometry which is complementary to the binding site. Examples of such interactions include antibody-antigen binding, enzyme-substrate binding, hormone-receptor binding, lymphokine-lymphokine receptor binding, and the like. The availability of such specific binding interactions is relied on in a variety of scientific, medical, and commercial processes, including immunoassays, therapeutic treatments, immunohistochemical methods, protein separations, reaction catalysis through transition state stabilization, and the like.

In many instances, it would be desirable to equip a specific binding protein or polypeptide with a constituent or functionality proximate the binding site, where the constituent will be able to provide a desired interaction with the target ligand. For example, it will often be desirable to provide constituents which are detectable or which have therapeutic or catalytic activity proximate a polypeptide binding site specific for a particular target ligand. By providing chemotherapeutic agents proximate the binding site (and absent from other locations) on specific binding proteins capable of binding diseased cells, chemotherapeutic activity may be enhanced while reducing toxic and other side effects which might otherwise be present. By providing a reporter molecule proximate a protein binding site (and absent from other locations) specific for a particular substance, assays may be provided where the presence of substrate provides for direct modulation of the observed signal from the reporter molecule.

Heretofore, methods for covalently binding active functionalities onto specific binding proteins, such as antibodies, have generally not been localized near the binding site. That is, binding has been achieved through amino acid side chains and carbohydrates which may be found at various locations on the protein surface, not limited to locations proximate the binding site. While enzymes have been modified to include functionalities, such as cofactors, proximate active sites, the localized binding of reporter molecules and chemotherapeutic agents proximate a protein binding site has not generally been taught. Moreover, methods for localized binding of active functionalities to proteins which have not been structurally characterized are generally unknown, regardless of the type of protein and type of active functionality.

In view of the above, it would be desirable to provide polypeptides having binding sites wherein chemotherapeutic agents or reporter molecules are bound proximate the binding site and substantially absent from the remainder of the polypeptide. It would be further desirable to provide methods for covalently binding active functionalities, including reporter molecules, chemotherapeutic agents, catalytic groups, reactive groups, and the like, proximate the binding site on polypeptides, even when the structure of the polypeptide is unknown.

2. Description of the Relevant Art

Immunotoxins comprising toxins and drugs covalently bound to antibodies specific for cellular receptors and other targets are known. See, e.g., U.S. Pat. Nos. 4,340,535; 4,368,149; 4,489,710; and 4,671,958. None of these patents, however, disclose site-specific binding of the toxins and drugs proximate the antibody binding site. European patent application 187 658 discloses antibodies covalently attached to activators. The antibodies bind to diseased sites within a host and the activators interact with an inactive substance within the host to produce an active substance. Binding of the activators is not limited to the antibody binding site. U.S. Pat. No. 3,817,752, describes homogeneous enzyme immunoassays employing detectable enzymes having hapten bound thereto. By exposing the enzymes to antibodies specific for the hapten, modulation of the enzyme activity can be achieved. The use of spin labels bound to enzymes to study enzyme activity is disclosed in Jones et al. (1973) Eur. J. Biochem. 34:28–40. Polyclonal antibodies have been generated with cofactor binding sites (Raso and Stollar (1975) Biochemistry 14:584–591). The generation of monoclonal antibodies having a cofactor binding site is described in Shokat et al. (1988) Angew. Chem. 100:1227–1229. The generation of affinity labels for antibody combining sites is described by Kohen et al. (1980) FEBS Lett. 11:427–431; Coetzl et al. (1970) Biochemistry 1267–1278; and Givol et al. (1971) Biochemistry 10:3461–3466. Site-directed mutagenesis has been used in conjunction with high resolution x-ray crystallography to analyze the structure of enzyme binding sites and the function of such sites in catalysis. Wilkinson et al. (1984) Nature 307:187–188; Craik et al. (1985) Science 228:291–297; Schultz et al. (1985) Biochemistry 24:6840–6848; Dalbadie-McFarland (1982) Proc. Natl. Acad. Sci. USA 79:6409–6413; and Sigal et al. (1984) J. Biol. Chem. 259:5327–5332. A cysteine in the active region of the enzyme papain has been modified with a flavin cofactor. Kaiser et al. (1984) Science 226:505–510. A thiol has been introduced into the enzymes staphylococcal nuclease and RNase S and subsequently derivatized with an oligonucleotide. Corey et al. (1987) Science 38:1401–1403. The active site serine of subtilisin has been chemically converted to a cysteine. Bender et al. (1966) J. Am. Chem. Soc. 88:3153–3154 and Koshland et al. (1966) Proc. Natl. Acad. Sci. USA 56:1606–1611.

SUMMARY OF THE INVENTION

According to the present invention, polypeptides are provided having active functionalities bound proximate a binding site, wherein the active functionalities are selected from the group consisting of reporter molecules and chemotherapeutic agents. The active functionalities are substantially absent from locations on the polypeptides other than proximate the binding site, and the presence of the functionalities does not substantially interfere with ligand binding to the binding site. Polypeptides will usually be in the form of antibodies or antibody fragments, where the antibodies are capable of binding particular target ligands, but other binding protein forms may also find use, including enzymes, hormones, lymphokines, lectins, avidin, membrane-bound cellular receptors, soluble receptors, viral coat proteins, structural proteins, and the like. Polypeptides having a binding site specific for an analyte of interest may be joined to reporter molecules such as fluorophores, chemiluminescers, bioluminescers, dyes, spin labels, flavins, piezoelectric molecules, biotin, redox active molecules, and the like, and will be useful for performing assays where the activity or detectability of the reporter molecule is directly modulated by binding to the analyte. Polypeptides having binding sites specific for diseased cells, tumor antigens, pathogens, and the like, may be joined to chemotherapeutic agents, such as toxins, bactericides, radical scavengers, radical generators, oxidants, alkylating agents, and the like, and will be useful for therapeutic treatment where the activity of the chemotherapeutic agent may be maximized and side reactivity minimized.

In a second aspect of the present invention, methods are provided for preparing detectable and chemotherapeutic polypeptides by post-translational modification of the polypeptides to introduce the active functionality of interest. The polypeptides may be natural or synthetic, where synthetic polypeptides include those prepared by both recombinant and solid phase synthesis techniques. The synthetic polypeptides may be modifications of an exemplary natural polypeptide where one or more amino acids are substituted or added proximate the binding site. By introducing rare or non-natural amino acids proximate the binding site and specifically attaching the active functionality through the rare or non-natural amino acid, non-localized binding of the functionality to sites in the polypeptide remote from the binding site may be minimized or avoided. The introduction of non-natural amino acids proximate the binding site is of particular interest as they can afford unique sites of reactivity which can assure that the active functionality being introduced will attach only at the location proximate the binding site.

When modifying natural polypeptides, i.e., those isolated from natural sources, the present invention provides a novel method which assures localized binding of the active functionality proximate the binding site. The method is useful even in the absence of structural information on the polypeptide. The method utilizes cleavable "affinity labels" which comprise a first reactive group cleavably bound to a ligand through a cleavable linker, where the ligand is specific for the binding site of the polypeptide. The first reactive group is capable of covalent binding to an amino acid side chain, usually a common side chain which will be expected to be present proximate the binding site (and elsewhere) on the polypeptide. By combining polypeptide with the affinity label, the ligand will form a complex with the binding site, thus carrying the first reactive group to a location proximate the binding site. The first reactive group may then be covalently attached to the amino acid side chain proximate the binding site. The reactive group is then cleaved from the polypeptide, and the ligand removed from the polypeptide. The polypeptide is left with a moiety (artifact) of the first reactive group covalently attached proximate the binding site. In some cases, the moiety itself may be the active functionality. More commonly, however, the moiety will serve as an attachment site for joining the active functionality of interest. The active functionality will be joined to the moiety attachment site under conditions which minimize or avoid entirely attachment elsewhere on the polypeptide. This method for attaching active functionality is not limited to reporter molecules and chemotherapeutic agents, and is useful for a wide variety of functionalities including catalytic functionalities and reactive functionalties, as described in copending application Ser. No. 07/273,455, filed on the same date as the present application, the disclosure of which is incorporated herein by reference.

BRIEF DESCRIPTION OF THE DRAWINGS

FIG. 1 illustrates the cleavable affinity labels used in Example 1 of the Experimental section.

FIG. 3 illustrates the strategy for introducing a thiol functionality into the binding site of MOPC 315 in Example 1.

FIG. 4 is a high pressure liquid chromatography profile of the tryptic digest of the heavy chain of Fab labeled with 2 (FIG. 1) monitored by UV absorbents (solid line) and radioactivity (dashed line), as described in Example 1.

FIG. 5 illustrates the DNP-containing esters utilized as substrates for reaction with thiolated Fab in Example 1.

FIG. 6 is an Eadie-Hofstee plot of cleavage of ester 14 by thiolated Fab labeled with 2 in Example 1.

FIG. 7 illustrates the results of a fluorescence quenching binding assay for DNP-glycine with fluorescein-Fab adduct (□) versus control with fluorescein plus underivatized Fab (▲). Fluorescence quenching experiments were carried at 10° C. using 492 nm for excitation and measuring emission at 521 nm. The fluorescein-Fab adduct was diluted with assay buffer (above) to 0.10 μM. Aliquots of 2,4-DNP-glycine were added and, after mixing, the fluorescence observed. Free N-fluoresceinthioureido-2-mercapthoethylamine and underivatized Fab, each at 0.10 μM, were treated in a similar experiment.

DESCRIPTION OF THE SPECIFIC EMBODIMENTS

Figure 2:
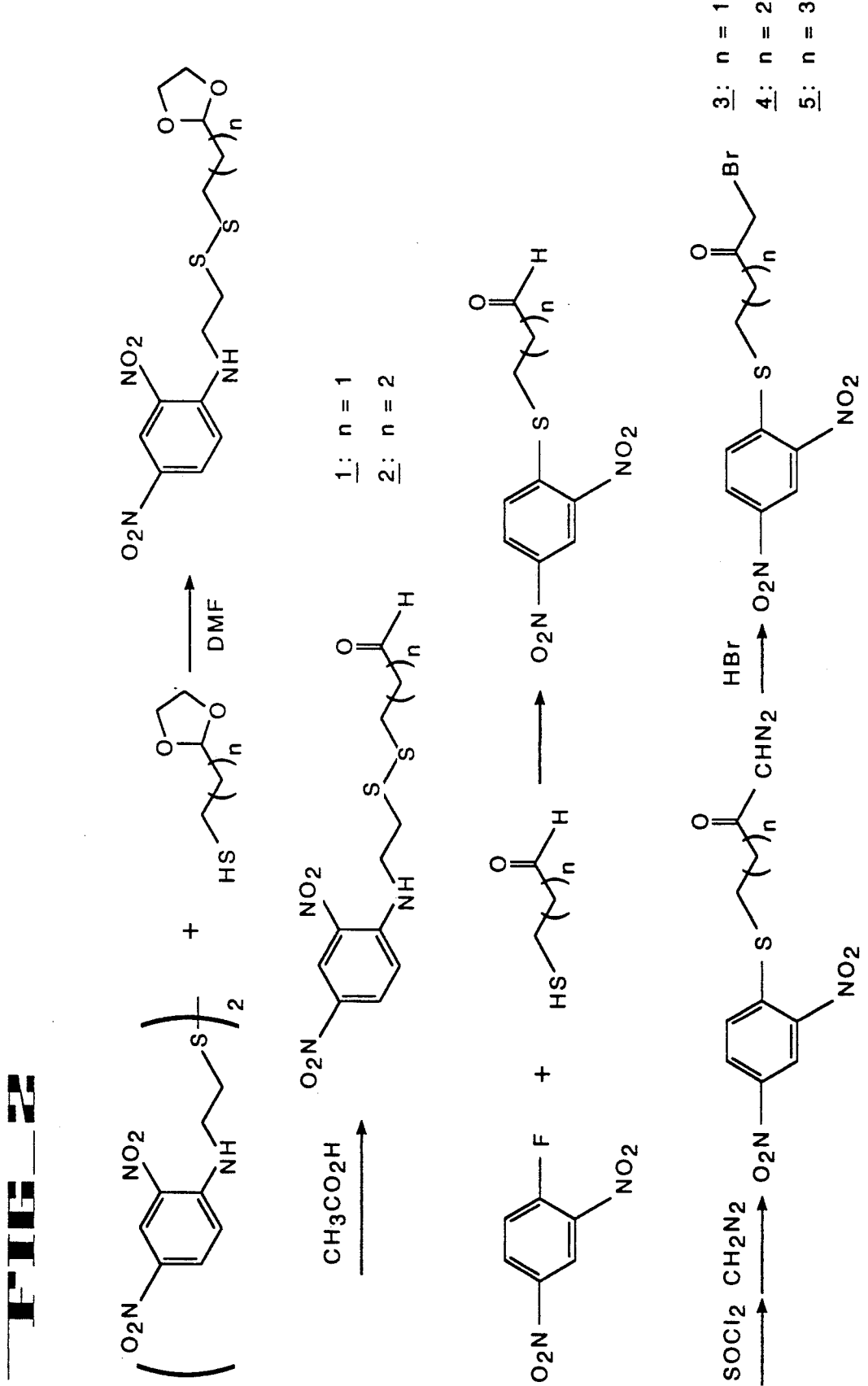
FIG. 2 outlines the methods for synthesizing the affinity labels of FIG. 1.

Novel polypeptides having binding sites capable of specifically binding a predetermined target ligand include at least one active functionality proximate the binding site. Locations on the polypeptide other than the binding site are substantially free from the active functionality so that the activity provided by the functionality will be localized to the binding site. The active functionality may be a reporter molecule, whereby the polypeptides will be useful in detecting the predetermined target ligand in a sample suspected of containing such ligand. Binding of the ligand to the polypeptide will modulate the activity provided by the active functionality, allowing detection and (optionally) quantitation of the substrate present in the sample. Alternatively, the active functionality may be a chemotherapeutic agent, whereby the polypeptide will be useful in treating a diseased state by site-specific drug delivery. Localization of the drug proximate the binding site will increase the efficiency of drug delivery by reducing the total drug dosage required. Side effects of the drug related to non-specific delivery will also be reduced.

The polypeptides of the present invention will have the following formula:

$$P-X-Y-Z,$$

wherein P, X, Y, and Z are defined as follows.

P is a polypeptide having a binding site capable of specifically binding the target ligand of interest. The polypeptide may be natural or synthetic, with the term natural generally referring to polypeptides isolated from living biological organisms, e.g., cell culture, animal tissue, plant sources, and the like, and the term synthetic generally referring to polypeptides produced by recombinant DNA methods and by chemical synthesis techniques, e.g., solid phase synthesis techniques. The polypeptides may be a single chain, or include multiple chains, and may be glycosylated or free from glycosylation. The size of the polypeptide is not critical, with polypeptides being in the range from 2 kilodaltons (kD) to 1000 kD, usually being in the range from 20kD to 200 kD. The polypeptides may be in the form of natural biological proteins, such as antibodies, enzymes, hormones, lectins, lymphokines, avidin (including streptavidin), membrane-bound cellular receptors, soluble receptors, viral coat proteins, structural proteins, and fragments thereof, as well as other proteins capable of specifically binding target molecules (ligands) which include analytes; biotin; diseased cells; tumor cells, normal cells, particularly classes of normal cells (e.g., T-lymphocytes); bacterial, fungal, and viral pathogens; parasites; mycoplasma; and the like. Of particular interest are antibodies which have been raised against the target ligand of interest.

Optionally, synthetic polypeptides may be prepared wherein the structure of a natural antibody (i.e., one which has been elicted against an immunogen) or other natural protein may be modified in a predetermined manner in order to facilitate introduction of the active functionality of interest, e.g., amino acids may be added, deleted, or substituted in order to provide a unique or rare attachment site proximate the binding site. Such modified polypeptides will generally retain the ability to mimic the naturally-occurring protein from which they have been derived and, in particular, will retain the ability to bind to the target ligand of interest. In the case of active proteins, such as enzymes, hormones, lymphokines, and the like, it will frequently be desirable to reduce or eliminate their activity so that the corresponding polypeptide is able to bind the target of interest without performing the function normally associated with the protein.

Alternatively, the polypeptides of the present invention may assume novel configurations which are not characteristic of known classes of biological proteins. In such cases, the polypeptides will be synthesized, either by recombinant techniques or by solid phase synthesis techniques, to provide a product having a desired sequence and structural configuration which will allow for binding of the polypeptide to the target ligand of interest.

Regardless of form and source, it is necessary that the polypeptide have a binding site with affinity for the target ligand of interest. The affinity will be at least about $10^{-3} M^{-1}$, usually being at least about $10^{-4} M^{-1}$, preferably being at least about $10^{-5} M^{-1}$, and more preferably being at least about $10^{-6} M^1$ or higher In the case of modified polypeptides, i.e., those which have changes in their amino acid sequence relative to a natural or exemplary protein, there should be no substantial loss of binding affinity as a result of the modification, and the modified polypeptide should generally meet the affinity levels just set forth even if some loss of affinity has occurred Polypeptides having the desired affinity are most easily prepared by raising antibodies, particularly monoclonal antibodies, against the target ligand or an analog thereof. The antibodies may be of any class including IgG, IgA, IgD, IgE, and IgM, although IgG and IgM will be the most common. Antibody fragments, particularly Fab fragments prepared by pepsin cleavage, will often be preferable to the use of intact antibody molecules. Methods for preparing antibodies and monoclonal antibodies to particular haptenic or antigenic target substrates are taught in Goding, *Monoclonal Antibodies: Principles and Practice*, Academic Press, 2nd Ed. (1986); Kennett et al. *Monoclonal Antibodies* (1980); U.S. Pat. Nos. 4,423,147; 4,381,292; 4,363,799; 4,350,683; and 4,127,124, the disclosures of which are incorporated herein by reference.

The binding site of the polypeptide is defined by a grouping of amino acids which are capable of specifically attaching to the target ligand of interest. The binding site will usually include from about 2 to 15 amino acids, more usually including from about 2 to 10 amino acids, where the amino acids may be contiguous or separated along the primary sequence of the polypeptide. When the amino acids are not contiguous, they will usually be brought together by the folding (secondary structure) of the polypeptide. The binding site will usually define a cavity or other three-dimensional structure which is complementary with a portion of the reactant or reactive intermediate which is being bound. In particular, the side chains of the amino acids within the binding site will interact with the particular structure (referred to as an epitope or determinant site in the case of antibody binding) on the target ligand.

X is an amino acid side chain proximate the binding site on the polypeptide P. The side chain X will normally be located outside of the three-dimensional structure of the binding site, but in some cases may lie within the binding site so long as presence of the active functionality does not substantially interfere with binding between the polypeptide and the target ligand. Generally, however, the side chain X will be located about the periphery of the binding site at a distance sufficiently close to provide a desired interaction (e.g., drug delivery or quenching of a fluorescent reporter molecule) between the active functionality and the target ligand. The distance between the side chain X and the binding site will usually be less than about 20 Å, more usually being less than about 10 Å, and preferably being less than about 5 Å.

The side chain X may be a natural amino acid side chain (i.e., a side chain of one of the naturally-occurring amino acids) or may be synthetic amino acid side chain (i.e., a side chain of an amino acid which does not occur in nature and which has been specifically introduced to the polypeptide by a synthetic preparatory method as described in more detail hereinbelow). In either case, the amino acid side chain will be sufficiently reactive to allow linking of an active functionality Z through a suitable linking group Y, as described in more detail hereinbelow.

When the side chain X is on a naturally-occurring amino acid, the side chain will usually be non-aliphatic, preferably being selected from the group of the basic side chains (those of lysine, arginine, and histidine), the acidic side chains (aspartate and glutamate), the aliphatic hydroxyl side chains (serine and threonine), thiol (cysteine), sulfide (methionine), phenol (tyrosine), and aminoindole (trytophan).

Preferably, the amino acid side chain will be present on a relatively rare amino acid chosen to be present proximate the polypeptide binding site, while being substantially absent from the remainder of the exposed surface of the polypeptide. Of course, such rare amino acids may be intentionally introduced to a location proximate the binding site (and deleted from locations away from the binding site) by modification of the primary structure of the polypeptide by synthetic techniques, as described in more detail hereinbelow. Whether or not an amino acid may be considered rare depends ultimately on the structure of the particular polypeptide. Any amino acid which is exposed to the surface of the polypeptide proximate the binding site, but is substantially absent elsewhere on the surface, can be considered rare. Usually, the rare amino acid will be present at 10 or fewer locations on the polypeptide P surface (other than proximate the binding site), preferably being present at 5 or fewer locations, and more preferably being present at no locations away from the binding site.

In some cases, it will be desirable to introduce unique amino acid side chains by providing synthetic amino acids proximate the binding site of the polypeptide. The use of synthetic amino acids allows the introduction of side chains with chemical reactivities distinct from those of the naturally-occurring amino acid side chains. In this way, localized binding of the active functionalities proximate the binding site can be assured. Particularly suitable synthetic amino acid side chains for covalent attachment of the active functionalities include aryl and alkyl amines (derivatized by alkylation of alkyl halides and α-haloketones, by reductive amination of aldehydes, by acylation of isocyanates or isothiocyanates, or by 1,4 additions of α,β unsaturated enones); aldehydes (derivatized by reductive amination of alkyl or aryl amines); carboxylic acid derivatives of the form C(O)A, where A=alkyl, aryl, or the like (derivatized by transacylation with alkyl or aryl amines); α,β unsaturated enones (derivatized by addition reactions with nucleophiles including amines and thiols); and the like.

Y is a linking group selected to provide the necessary covalent bridge between the amino acid side chain X and a reactive group on the active functionality Z. Exemplary reactive groups include thiol, disulfide, ester, aldehyde, α-haloketone, diazonium, isocyanate, α,β unsaturated ketones, and the like. The nature of the linking group is not critical, but it is preferred that the chemistry used to introduce the linking group be selective for the desired side chain X in order to avoid linkage of the active functionality to other amino acid side chains. The length of the linking group Y is not critical and may vary between about 1.5 Å and 25 Å, usually varying between about 5 Å and 12 Å. Alternatively, the linking group will be formed from a bifunctional cross-linking agent. The binding provided by the linking group should be sufficiently stable to withstand purification procedures after the binding is completed as well as withstanding the conditions of use. In some cases, however, it might be desirable to provide biologically labile and/or chemically labile linking groups which will be degraded under preselected conditions. For example, immunotoxins comprising toxins coupled to antibodies frequently require that the toxin be cleavable at the surface of a bound cell to allow invagination of the toxin. General techniques for binding molecules to amino acid side chains are well described in the patent and scientific literature. See, for example, Cuatrecasas et al. (1969) J. Biol. Chem. 244:4316; Givol et al. (1971) Biochemistry 10:3461; U.S. Pat. Nos. 4,340,535; 4,368,149; 4,489,710; and 4,671,958; and European patent application 187 658, the disclosures of which are incorporated herein by reference.

Exemplary linking groups Y may be formed directly between amino acid side chains X and reactive groups on the active functionality Z as follows:

| Linking Group Y | X (or moiety thereon) | Reactive Group on Z |
|---|---|---|
| $-CH_2-\overset{H}{N}-CH_2-$ (amine) | aldehyde | amine/NaBH$_3$ |
| —S—S— (disulfide) | S—SR or SH | SH or S—SR |
| azobenzene | tyrosine | aryldiazonium |
| amine | aryl or alkylamine | α-haloketone |
| thiourea | aryl or alkylamine | isothiocyanate |
| 1,4-Michael adduct | thiol or aryl or alkylamine | α,β-enone |
| amide | aryl or alkylamine | N-hydroxy succinimide ester |
| amide | aryl or alkylamide | anhydride |

Alternatively, bifunctional cross-linking agents may be used to introduce linking groups Y between the amino acid side chain X and the active functionality Z. Exemplary cross-linking agents are as follows.

| Cross-Linking Agent | Reactive Group on Z |
|---|---|
| 1. 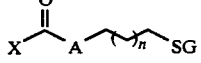 | —OH, —NHR |
| 2. 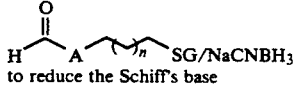 to reduce the Schiff's base | —NHR |
| 3. $S=C=N\sim\!\!\!\sim_n\text{SG}$ | —NHR |
| 4. $O=C=N\sim\!\!\!\sim_n\text{SG}$ | —SH |
| 5. Nitration with HNO$_3$/H$_2$SO$_4$ followed by reduction with NaBH$_4$ followed by reaction with 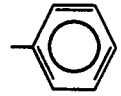 | 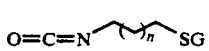 |

| Cross-Linking Agent | Reactive Group on Z |
|---|---|
| 6. 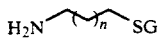 | 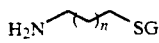 |
| 7.  |  | where G is a suitable protecting group, e.g., thiopyridyl or acyl; A is $CH_2$, O, or NH; R is aryl or hydrogen; and X is anhydride, N-hydroxysuccinimide ester, or other active acyl group.

The active functionality Z will be a molecule selected from the group consisting of reporter molecules and chemotherapeutic agents. The size of the active functionality molecule is not critical, but will generally be in the range from about 100 to 2000 daltons (D), more usually being in the range from about 200 to 1000 D. The structure of the active functionality will vary widely, depending on its type and the intended use, but will necessarily include a reactive group which will be available to covalently bind to the polypeptide P either directly or via a bifunctional cross-linking agent. Active functionalities which in their natural state do not include suitable reactant groups will have to be modified to provide for such groups in a manner which does not interfere with their desired activity. Suitable reactive groups on the active functionality are set forth above.

Reporter molecules and compounds are selected to provide a detectable signal where the strength or other characteristic of the signal may be affected or modulated by binding of the polypeptide to the target ligand (analyte). Suitable reporter molecules include chromogens (e.g., dyes and fluorophores), chemiluminescers, bioluminescers, spin labels, flavins, piezoelectric molecules, biotin, and the like. Numerous suitable reporter molecules are described in U.S. Pat. No. 4,366,241, the disclosure of which is incorporated herein by reference.

Suitable chromogens will include molecules and compounds which absorb light in a distinctive range so that a color may be observed, or emit light when irradiated with radiation of a particular wavelength or wavelength range, e.g., fluorescers.

A wide variety of suitable dyes are available, being primarily chosen to provide an intense color with minimum absorption by their surroundings. Illustrative dye types include quinoline dyes, triarylmethane dyes, acridine dyes, alizarin dyes, phthaleins, insect dyes, azo dyes, anthraquinoid dyes, cyanine dyes, phenazathionium dyes, and phenazoxonium dyes.

A wide variety of fluorescers may be employed either by themselves or in conjunction with quencher molecules. Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthene, 7-hydroxycoumarin, phenoxazine, salicylate, strophanthidin, porphyrins, triarylmethanes and flavin.

Individual fluorescent compounds which have functionalities for linking or which can be modified to incorporate such functionalities include dansyl chloride, fluoresceins such as 3,6-dihydroxy-9-phenylxanthhydrol, rhodamineisothiocyanate, N-phenyl 1-amino-8-sulfonatonaphthalene, N-phenyl 2-amino-6-sulfonatonaphthalene, 4-acetamido-4-isothiocyanatostilbene-2,2'-disulfonic acid, pyrene-3-sulfonic acid, 2-toluidinonaphthalene-6-sulfonate, N-phenyl, N-methyl 2-aminonaphthalene-6-sulfonate, ethidium bromide, stebrine, auromine-0, 2-(9'-anthroyl)palmitate, dansyl phosphatidylethanolamine, N,N'-dioctadecyl oxacarbocyanine, N,N'-dihexyl oxacarbocyanine, merocyanine, 4-(3'-pyrenyl)butyrate, d-3-aminodesoxyequilenin, 12-(9'-anthroyl)stearate, 2-methylanthracene, 9-vinylanthracene, 2,2'-(vinylene-p-phenylene)bisbenzoxazole, p-bis[2-(4-methyl-5-phenyloxazolyl)]benzene, 6-dimethylamino-1,2-benzophenazin, retinol, bis(3'-aminopyridinium) 1,10-decandiyl diiodide, sulfonaphthylhydrazone of hellibrienin, chlorotetracycline, N-(7-dimethylamino-4-methyl-2-oxo-3-chromenyl) maleimide, N-[p-(2-benzimidazolyl)phenyl]maleimide, N-(4-fluoranthyl) maleimide, bis(homovanillic acid), resazarin, 4-chloro-7-nitro-2,1,3-benzooxadiazole, merocyanine 540, resorufin, rose bengal, and 2,4-diphenyl-3(2H)-furanone.

Desirably fluorescers should absorb light above about 300 nm, preferably above 350 nm and more preferably above about 400 nm, usually emitting at wavelengths greater than 10 nm higher than the wavelength of the light absorbed. It should be noted that the absorption and emission characteristics of the bound dye may differ from the unbound dye. Therefore, when referring to the various wavelength ranges and characteristics of the dyes, it is intended to indicate the dyes as employed and not the dye which is unconjugated and characterized in an arbitrary solvent.

Fluorescers are generally preferred to absorptive dyes to the extent that a single fluorescer can provide for multiplication of a signal. By irradiating a fluorescer with light, one can obtain a plurality of emissions. Thus, a single label can provide for a plurality of measurable events.

Detectable signal may also be provided by chemiluminescent and bioluminescent sources. Chemiluminescent sources include a compound which becomes electronically excited by a chemial reaction and may then emit light which serves as the detectible signal or donates energy to a fluorescent acceptor. A diverse number of families of compounds have been found to provide chemiluminescence under a variety of conditions. One family of compounds is 2,3-dihydro-1,-4-phthalazinedione. The most popular compound is luminol, which is the 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, e.g., p-nitrophenyl and a peroxide, e.g., hydrogen peroxide, under basic conditions. Alternatively, luciferins may be used in conjunction with luciferase or lucigenins to provide bioluminescence.

Spin labels are provided by reporter molecules with an unpaired electron spin which can be detected by electron spin resonance (ESP) spectroscopy. Exemplary spin labels include organic free radicals, transition metal complexes, particularly vanadium, copper, iron, and manganese, and the like. An exemplary spin label is nitroxide free radical.

Chemotherapeutic agents will be selected depending on the diseased state which is being treated as well as on the nature of the target ligand. Such agents may be intended to kill diseased cells of the host, kill pathogens, inhibit cellular proliferation, provide hormone therapy, or provide a wide variety of other beneficial interactions between the agent and the target ligand. Exemplary chemotherapeutic agents include toxins, toxin fragments, bactericides, radical scavengers, radical generators, alkylating agents, neurotransmitters, radionuclides, antiviral compounds, antifungal compounds, antineoplastic agents, antimycoplasmal agents, heavy metals, and the like. A list of suitable drugs is provided in Table 1.

TABLE 1

| Drug Type | Examples |
|---|---|
| Antibacterials | Sulfanilamide |
| | Polymyxin |
| | Chloramphenicol |
| | Aminoglycosides: |
| | Streptomycin |
| | Neomycin |
| | Kanamycin |
| | Amikacin |
| | Gentamicin |
| | Tobramycin |
| | Streptomycin B |
| | Spectinomycin |
| | Ampicillin |
| Antivirals | Acyclovir |
| | Vir A |
| | Symmetrel |
| Antifungals | Nystatin |
| Antineoplastics | Adriamycin |
| | Cerubidine |
| | Bleomycin |
| | Alkeran |
| | Valban |
| | Oncovin |
| | Fluorouracil |
| Radiopharmaceuticals | $I^{125}$ |
| | $I^{131}$ |
| | $^{99m}Tc$ (Technetium) |
| Heavy Metals | Barium |
| | Gold |
| | Platinum |
| Antimycoplasmids | Tylosine |
| | Spectinomycin |
| Toxins | Ricin |
| | Ricin A chain |
| | Diptheria toxin |
| | Diptheria toxin A chain |
| | Abrin |
| | Modeccin |

The polypeptides of the present invention are generally prepared by a two-step technique where the polypeptide (without the active functionality) is first produced and the active functionality is then site-specifically introduced proximate the binding site of the polypeptide. The polypeptides may be obtained from natural sources, such as cell cultures, animal tissues, plant sources, and the like, or may be produced synthetically as described in more detail hereinbelow. Most commonly, the polypeptides will be antibodies or antibody fragments elicited against the target ligand of interest (or an analog thereof) in a conventional manner.

The target ligand of interest may be utilized as an antigen, or if sufficiently small, may be attached to a suitable immunogen for providing antigenicity. Once the antigenic target ligand is obtained, polyclonal antibodies specific for the substrate may be produced by in vitro or in vivo techniques. In vitro techniques involve in vitro exposure of lymphocytes to the antigenic target substrates, while in vivo techniques require the injection of the antigenic target substrates into a wide variety of vertebrates. Suitable vertebrates are non-human, including mice, rats, rabbits, sheep, goats, and the like. Target substrates smaller than about 10 kD, particularly smaller than about 6 kD, will usually be joined to a larger molecule to elicit the desired immune response. With in vivo techniques, the immunogens are injected into the animal according to a predetermined schedule, and the animals are bled periodically with successive bleeds having improved titer and specificity. The injections may be made intramuscularly, intraperitoneally, subcutaneously, or the like, and an adjuvant, such as incomplete Freund's adjuvant, will be employed.

If desired, monoclonal antibodies can be obtained by preparing immortalized cell lines capable of producing antibodies having the desired specificity. Such immortalized cell lines may be produced in a variety of ways. Conveniently, a small vertebrate, such as a mouse, is hyperimmunized with the desired antigen by the method just described. The vertebrate is then killed, usually several days after the final immunization, the animal's spleen removed, and the spleen cells immortalized. The manner of immortalization is not critical. Presently, the most common technique is fusion with a myeloma cell fusion partner, as first described by Kohler and Milstein (1976) Eur. J. Immunol. 6:511–519. Other techniques include EBV transformation, transformation with bare DNA, e.g., oncogenes, retroviruses, etc., or any other method which provides for stable maintenance of the cell line and production of monoclonal antibodies.

When employing fusion with a fusion partner, the manner of fusion is not critical and various techniques may be employed. Conveniently, the spleen cells and myeloma cells are combined in the presence of a nonionic detergent, usually polyethylene glycol, and as Dulbecco's Modified Eagle's medium, for a few minutes. At the end of the fusion, the non-ionic detergent is rapidly removed by washing the cells, the few cells are promptly dispensed in small culture wells (usually in a microtiter plate) at relatively low density, ranging from about 1 to $5 \times 10^5$ per well, in a selective medium chosen to support growth of the hybrid cells while being lethal to the myeloma cells. Usually, the myeloma cell line has been mutated to be sensitive to a lethal agent, typically being HAT-sensitive.

After sufficient time, usually from one to two weeks, colonies of hybrids are observed and plates containing hybrid positive wells are identified. The plates and wells having only one colony per well are selected, and supernatants from these wells are tested for binding activity against the target ligand. Once the positive hybridomas are identified, the cell line can be maintained as a viable culture and/or by lyophilization and frozen storage.

Once the hybridomas have been selected, monoclonal antibodies may be isolated from the supernatants of the growing colonies. The yield of antibodies obtained, however, is usually low. The yield may be enhanced by various techniques, such as injection of the hybridoma cell line into the peritoneal cavity of a vertebrate host which accepts the cells. Monoclonal antibodies may then be harvested from the ascites fluid or from the blood. Proteinaceous and other contaminants will usually be removed from the monoclonal antibodies by conventional techniques, e.g., chromatograph, gel filtration, precipitation, extraction, or the like.

Synthetic and recombinant techniques for producing the polypeptides of the present invention will usually start with an exemplary amino acid sequence which is characteristic of a protein which is known to bind the target ligand with the requisite affinity. Such exemplary amino acid sequences may be derived from enzymes which are known to bind to a target ligand of interest or from antibodies which have been raised against the target substrates as described above. Natural receptors and ligands such as hormones, lymphokines, lectins, avidin (including streptavidin), proteins of the major histocompatibility complex (MHC), T-cell receptors, G proteins, neurotransmitter receptors, DNA binding proteins, e.g., repressors, and the like will also find use in defining binding sites of interest which may be incorporated into synthetic polypeptides.

Synthetic methods may be utilized for preparing polypeptides having fewer than about 200 amino acids, usually having fewer than about 150 amino acids, and more usually having 100 or fewer amino acids. The synthetic preparation methods, as described in more detail below, are particularly convenient for allowing the insertion of synthetic (non-natural) amino acids at a desired location proximate the binding site of the polypeptide, but suffer from low yields and lack of glycosylation when compared to biological synthesis techniques.

Suitable synthetic polypeptide preparation methods may be based on the well-known Merrifield solid-phase synthesis method where amino acids are sequentially added to a growing chain (Merrifield (1963) J. Am. Chem. Soc. 85:2149-2156). Automated systems for synthesizing polypeptides by such techniques are now commercially available from suppliers such as Applied Biosystems, Inc., Foster City, Calif. 94404; New Brunswick Scientific, Edison, N.J. 08818; and Pharmacia, Inc., Biotechnology Group, Piscataway, N.J. 08854.

For the preparation of larger and/or glycosylated polypeptides, recombinant preparation techniques are usually preferred. Such recombinant techniques involve the expression in cultured cells of recombinant DNA molecules encoding the desired polypeptide amino acid sequence. The DNA sequence may itself be synthetic or alternatively be modified from a natural source, i.e., the gene of an exemplary antibody, enzyme, lymphokine, hormone, or other protein. Synthetic DNA sequences (polynucleotides) may be synthesized by well-known techniques. For example, short-single stranded DNA fragments may be prepared by the phosphoramidite method described by Beaucage and Carruthers (1981) Tett. Letters 22:1859-1862. A double-stranded fragment may then be obtained by either synthesizing a complementary strand and annealing the strands together under appropriate conditions or by adding the complementary strand using DNA polymerase with an appropriate primer sequence. Conveniently, automated equipment for preparing the synthetic DNA sequences are available from the suppliers listed above as providing synthetic polypeptide equipment. Alternatively, the desired DNA sequence may be obtained from a suitable cDNA or genomic library obtained from a cell line expressing the exemplary protein of interest. For example, the gene expressing a monoclonal antibody of interest may be isolated from the hybridoma cell line expressing such antibody. The gene may then be modified as described in more detail hereinbelow to substitute or add amino acid(s) capable of binding the active functionality of interest. The techniques for isolating antibody genes from hybridoma cell lines are well described in the scientific literature. See, for example, Gearhart et al. (1983) Proc. Natl. Acad. Sci. USA 80:3439-3443.

The natural or synthetic DNA fragments coding for the desired catalytic or reactive polypeptide will be incorporated in DNA constructs capable of introduction to and expression in an in vitro cell culture. The DNA constructs may be suitable for replication in a unicellular host, such as yeast or bacteria, but will frequently be intended for introduction into and integration within the genome of cultured mammalian or other eukaryotic cell lines. DNA constructs prepared for introduction into bacteria or yeast will include a replication system recognized by the host, the DNA fragment encoding the polypeptide of interest, transcriptional and translation initiation regulatory sequences joined to the 5'-end of the DNA sequence, and transcriptional and translational termination regulatory sequences joined at the 3'-end of the DNA sequence. The transcriptional regulatory sequences will include a heterologous promoter which is recognized by the host. Conveniently, available expression vectors which include replication system and transcriptional and translational regulatory sequences together with an insertion site for the DNA sequence to be expressed may be employed.

When starting with isolated genes encoding the exemplary protein, usually an antibody, enzyme, lymphokine, hormone, or a fragment thereof, it will usually be desirable to modify the gene to substitute or add amino acid(s) through which the active functionality will be bound within or near the binding site. A variety of methods for altering the natural gene sequence to provide such substitutions or additions are known and amply described in the patent and scientific literature. See, for example, *Molecular Cloning: A Laboratory Manual* (Maniatis et al., eds.) Cold Spring Harbor Laboratory, Cold Spring Harbor, N.Y. (1982) and Guide to *Molecular Cloning Techniques* (Berger and Kimmel, eds.) Methods in Enzymology, Vol. 152, Academic Press, Inc., Orlando, Fla. (1987). Particular techniques for providing such alterations in the gene include site-directed mutagenesis as described by Kunkel et al. (1985) Nucleic Acids Res. 13:8764 and cassette mutagenesis as described by Wells et al. (1985) Gene 34:315-323. The altered gene may then be expressed in cell culture as described above and the modified polypeptide obtained by conventional purification techniques.

A second method may be employed for the substitution of synthetic (non-natural) amino acids in an exemplary protein encoded by an unmodified protein gene. The gene is altered, as described above, to replace an amino acid codon at the desired location proximate the binding site with a nonsense codon differing from the gene's termination codon. Conveniently, oligonucleotide-directed mutagenesis can be employed for such substitution. A suppressor tRNA, directed against the nonsense codon, is chemically or enzymatically acylated with the desired synthetic amino acid and added to an in vitro transcription/translation system programmed to express the altered DNA sequence. The synthetic amino acid will be inserted at the location of the nonsense codon. The approach, of course, would work with natural amino acids as well, but would be more cumbersome than simple alteration of the DNA sequence to encode the desired natural amino acid.

The desired unique codon must not encode a natural amino acid insertion site (natural tRNA recognition site), and a suitable codon is a TAG termination or amber codon. Any mutation in a gene that generates a termination codon (TAG, TAA, or TGA) leads to premature termination of polypeptide synthesis as a consequence of the inability of the naturally-occurring tRNA to bind and compete with the release factors. Such altered genes will, of course, have to utilize one of the two alternate termination codons. This approach is particularly advantageous in that alternate amino acid substitutions can be obtained by preparation of different synthetic amino acids at the aminoacylation stage.

Mutations in the anti-codon loop of a number of tRNA molecules leads to an amber suppressor tRNA. See, e.g., Steege and Soll, in: *Biological Regulation and Development*, Vol. I, (Goldberger, ed.) Plenum Press (1978). Amber suppressors, characterized by a 5'-CUA-3' anti-codon loop, no longer respond to codons recognized by their wild-type counterparts, but instead insert amino acids only in response to amber codons (UAG). The desired tRNA carrying a synthetic amino acid can be generated by anti-codon loop replacement, as described by Bruce et al. (1982) Proc. Natl. Acad. Sci. USA 79:7127-7131. Alternatively, a gene encoding the tRNA carrying the synthetic amino acid may be synthesized and expressed in a suitable expression system or the suppressor tRNA can be generated by runoff transcription. The chemically or genetically constructed suppressor tRNA must then be aminoacylated with the synthetic amino acid to be incorporated into the polypeptide of the present invention. A suitable chemical acylation method which utilizes N-blocked aminoacyl pCpA dinucleotide synthesized via carbonyldiimidazole mediated coupling of N-blocked amino acids with protected pCpA-OH, is condensed with an abbreviated tRNA in the presence of T4 RNA ligase. Heckler et al. (1984) Tetrahedron 40:87-94. A suitable prokaryotic in vitro transcription/translation system is described in Pratt, in: *Transcription and Translation, A Practical Approach* (Hames and Higgens, eds.) IRL Press, Washington (1984).

The recombinant production of antibodies is taught in a number of recent patent applications, including EPO 8430268.0; EPO 85102665.8; EPO 5305604.2; PCT/GB85/00392; EPO 85115311.4; PCT/US86/002269; and Japanese application 85239543, the disclosures of which are incorporated herein by reference. See also U.S. Pat. No. 4,518,584, the disclosure of which is incorporated herein by reference, which describes site-directed mutagenesis of mammalian proteins.

Once the polypeptide has been obtained by any of the techniques described above, the active functionality will be covalently attached to an amino acid side chain proximate the binding site of the polypeptide, either directly or through a bifunctional linker as described above. By providing a rare or synthetic amino acid proximate the binding site, the linking group will be localized at the binding site and will be substantially absent from locations on the polypeptide other than proximate the binding site. Alternately, a novel affinity labeling technique may be employed for site-specific introduction of a linking group to the side chains of even common amino acids, as described in more detail hereinbelow.

Linking groups and active functionalities may also be introduced to the polypeptides by a novel technique employing cleavable affinity-labeling reagents. Such reagents are obtained by joining cleavable reactive groups to affinity labels, e.g., haptens specific for the protein binding site. By binding the cleavable affinity labels to the protein at the binding site, and subsequently covalently attaching the free end of the reactive group to an amino acid side chain proximate the binding site, the reactive group can be cleaved from the hapten and the hapten removed from the protein, leaving the reactive group in place on the polypeptide. Useful amino acid side chains for attachment of the affinity-labeling reactive groups include carboxylate (aspartate and glutamate), primary amine (lysine), imidazole (histidine), phenol (tyrosine), and thiol (cysteine). The reactive group moiety remaining after cleavage may itself comprise the active functionality, particularly a catalytic or reactive functionality as defined in greater detail in co-pending application Ser. No. 07/273,455, previously incorporated herein by reference. More often, however, the reactive group moiety on the polypeptide will be useful as an attachment site for covalently attaching the active functionality. The covalent attachment methods described hereinabove will generally be useful for attaching functionalities, including reporter molecules and chemotherapeutic agents, to reactive groups introduced by affinity labeling. Specific methods for synthesizing such affinity labels and attaching them to an antibody combining site are taught in Example 1 in the Experimental section hereinafter. Such cleavable affinity labels are particularly suitable for selectively modifying polypeptides which have not been structurally characterized.

The introduction of thiols (useful in forming disulfide bonds to an active functionality) to the binding site of a polypeptide may be accomplished using affinity labels as follows. The affinity label may be a thiol ester or a disulfide reactive group bound to the hapten, and cleavage of the label after site-specific derivatization will incorporate a free thiol at the binding site. A thiol ester can be cleaved with hydroxylamine while a disulfide can be reduced with dithiothreitol. The disulfides are reduced under mild conditions chosen to avoid disulfides buried within the protein. Another functionality suitable for cleavable linkage is acetal, which would lead to a protein-bound aldehyde moiety that could be derivatized by reductive amination. However, the acidic conditions required for cleavage could lead to inactivation of acid-sensitive proteins. An azobenzene crosslink could be cleaved reductively to give an aromatic amine, which could then be selectively derivatized at low pH.

The choice of the reactive group in the affinity-labelling reagents is governed by a number of factors. The reactive linking group should react slowly enough so that it will react primarily at or near the binding site of the protein after equilibrium is established. The group may react with more than one type of amino acid residue, which is advantageous for maximizing the likelihood of successful derivatization. It is disadvantageous in that it can complicate the characterization of the labeled protein. Ideally, a unique residue on the polypeptide should be modified to give a homogeneous adduct. Another important consideration is the synthesis of the labeling reagents. It should be possible to easily vary the length of the reagent in order to optimize incorporation of label into the protein. The affinity label should also be easily synthesized in radiolabeled form, for ease in quantitating label incorporation. Finally, the label should be stable to subsequent protein manipulation conditions, including the degradative methods used in protein sequence determination.

Two preferred reactive groups which may be introduced using affinity labels are diazoketones and aromatic azides. These groups can be transformed into reactive species in the protein binding site by photochemical irradiation and therefore have the advantage that they can be specifically activated in the binding site of a protein. Several other reactive chemical functionalities are also suitable. Diazonium groups react specifically with the phenolic side chain of tyrosine. Epoxide groups react with nucleophilic side chains including primary amines (lysine) and carboxylates (aspartate and glutamate). Aldehydes react with the primary amine side chain of lysine to form Schiff base intermediates which can be reduced with sodium cyanoborohydride. The use of tritiated $NaCNB^3H_3$ leads to tritium incorporation, facilitating the characterization of the labeled protein. Finally, α-bromoketones are versatile affinity-labeling reagents. Their reactivity is sufficiently slow that they can label proteins nearly stoichiometrically in their binding sites. Moreover, they react with a number of nucleophilic side chains, including carboxylate, primary amine (lysine), imidazole (histidine), and phenol (tyrosine).

The polypeptides of the present invention having attached reporter molecules will be useful in performing assays for analytes in biological and other samples. In general, the assays will be useful for detecting the presence of the target ligands of the polypeptide, i.e., the analyte will be the target ligand. Presence of the target ligand in a sample may be detected and optionally quantitated based on an observed change in the signal provided by the reporter molecule, usually a reduction in the strength of the signal caused by an interaction between the reporter molecule and the bound target ligand. In specific systems, the signal may be calibrated in order to provide quantitative or semi-quantitative measurement of a desired analyte.

The compositions of the present invention will be particularly advantageous in that they allow the performance of non-competitive, homogeneous assays. As the polypeptides can directly bind the target ligand and provide a signal which is inversely proportional to the concentration of target ligand, no ligand displacement is necessary. Moreover, no separation step is required as the signal modulation can be achieved in the sample medium.

The present invention also allows for the use of secondary binding systems in the performance of assays. By attaching intermediate binding species, e.g., biotin, a hapten, or the like, to the polypeptide proximate the binding site, the reporter molecule can be introduced to the system through a binding protein specific for the intermediate binding species, e.g., avidin or antibody specific for the hapten. Thus, biotin and haptens are considered reporter molecules for the purpose of the present invention.

The polypeptides of the present invention having attached chemotherapeutic agents will be useful in providing therapeutic treatment of humans and other animals. In particular, polypeptides bound to cellular toxins may be used to treat different forms of cancer where the neoplastic cells are characterized by a unique tumor antigen which allows specific attachment of the polypeptides, usually through an antibody directed against the tumor antigen. Additionally, bacterial infection may be treated by antibodies specific for the bacteria bound to a suitable bactericide, such as an antibiotic.

The polypeptides of the present invention having bound chemotherapeutic agents may be incorporated in conventional pharmaceutical formulations for administration to humans and other animals. Such pharmaceutical compositions should contain a therapeutic dosage of the polypeptide in a suitable pharmaceutically-effective carrier. The pharmaceutical carrier may be any compatible, non-toxic substance suitable to deliver the polypeptides to the patient. Sterile water, alcohols, fats, waxes, and inert solids may be used as a carrier. Pharmaceutically-acceptable adjuvants, buffering agents, dispersing agents, and the like, may also be incorporated in the pharmaceutical compositions of the present invention. Such pharmaceutical compositions may contain a single polypeptide according to the present invention, or may contain two or more such polypeptides. Additionally, other therapeutically active ingredients may be included. Such "cocktails" including two or more polypeptides and/or active ingredients having different specificities and/or different therapeutic activities may be beneficial under a variety of circumstances.

The pharmaceutical compositions of the present invention will be suitable for oral or parenteral administration, particularly for parenteral administration, including subcutaneous, intramuscular, and intravenous injection. A typical pharmaceutical composition for intramuscular injection would contain 1 ml sterile buffered water and 50 mg of the polypeptide composition of the present invention. Typical composition for intravenous and fusion would contain about 250 ml of sterile Ringer's solution, and 150 mg of monoclonal antibody. Actual methods for preparing parenterally administratable compositions are known to those skilled in the art and are amply described in the patent, medical and scientific literature. Specific reference is made to *Remington's Pharmaceutical Science*, 15th Ed., Mack Publishing Company, Easton, Pa. (1980), the disclosure of which is incorporated herein by reference. Polypeptides of the present invention can be lyophilized for storage and reconstituted in a suitable carrier prior to use. This technique has been shown to be effective with a wide variety of antibodies and other proteins. It will be appreciated by those skilled in the art that lyophilization and reconstitution can lead to varying degrees of antibody activity loss and that the amount of the antibodies or other polypeptides in the pharmaceutical compositions may have to be adjusted to compensate for such loss.

The following examples are offered by way of illustration, not by way of limitation.

EXPERIMENTAL

1. Introduction of Active Functionality to Antibody Using Affinity Label

The following studies were carried out on the IgA MOPC315, which binds substituted 2,4-dinitrophenyl (DNP) ligands with association constants ranging from $5 \times 10^4$ to $10^6 M^{-1}$ (Haselkorn et al. (1974) Biochemistry 13:2210). Although a three-dimensional structure is not available, the antibody combining site has been characterized by spectroscopic methods (UV, fluorometry, NMR), chemical modification, and amino acid sequencing of the variable region. Moreover, earlier affinity-labeling studies with reagents of varying structures (Givol and Wilcheck (1977) Meth. Enzy. 46:479; Givol et al. (1971) Biochemistry 10:3461; and Strausbauch et al. (1971) Biochemistry 10:4342) defined a number of reactive amino acid side chains in the vicinity of the combining site.

Cleavable tethers were incorporated into affinity labels specific for the MOPC315 combining site, as shown in FIG. 1. These affinity-labeling reagents contain the DNP group linked to electrophilic aldehyde or α-bromoketone groups via cleavable disulfide or thiophenyl linkages. Covalent attachment of the label to the antibody, followed by cleavage of the crosslink and removal of the free ligand, results in site-specific incorporation of a free thiol into the antibody combining site. The geometry of the affinity-labeling reagents 1–5 varies with regard to the distance between the DNP group and electrophilic moiety since the position of a nucleophilic lysine, histidine, or tyrosine side chain is not precisely known. The syntheses of affinity labels 1–5 are outlined in FIG. 2, and are described in detail hereinbelow.

(N-2,4-Dinitrophenyl)-2-aminoethyl 2-(1,3-dioxolanyl)-ethyl disulfide 6

Affinity labels 1 and 2 were prepared as follows:

To a suspension of N,N'-bis-(2,4-dinitrophenyl)-cystamine (Chan et al. (1979) Phosphorous Sulfur 7:41) (4.84 g, 10 millimoles) in dimethylformamide (200 ml) with triethylamine (50 μl) was added 2-(2-mercaptoethyl)-1,3-dioxolane (2.45 g, 18 millimoles), and the mixture was stirred at 60° C. for 24 hours. Hydrogen peroxide (2 ml of a 30% solution) was added and the dimethylformamide was removed in vacuo.

The residual oil was dissolved in methylene chloride (100 ml). The methylene chloride layer was washed with water (3×5 ml), dried over MgSO$_4$, and concentrated in vacuo to an oil. Silica gel column chromatography with 3:2 hexanes: ethyl acetate (R$_f$—0.31) afforded 6 (1.37 g, 3.65 millimoles, 20%) as an orange oil. IR (thin film): 3353, 2923, 1623, 1525, 1342, 1138 cm$^{-1}$; $^1$H-NMR, CDCl$_3$: δ 2.08 (m,2H),2.82 (t,2H,J=7.1 Hz), 3.00 (t,2H,J=6.6 Hz), 3.8–4.0(m,6H), 4.95 (t,1H,J=4.3 Hz), 7.00(d, 1H,J=9.5 Hz), 8.30 (d, 1H,J=9.6 Hz), 8.80 (s, 1H), 9.16 (d, 1H, J=2.6 Hz); mass spectrum (EI) 375 (M+). Anal. Calcd. for C$_{13}$H$_{17}$N$_3$O$_6$S$_2$: C, 41.60; H, 4.53; N, 11.20; S, 17.07. Found: C, 41.57; H, 4.67; N, 11.10; S, 16.99.

(N-2,4-Dinitrophenyl)-2-aminoethyl 3-oxopropyl disulfide 1

A solution of dioxane 6 (0.50 g, 1.33 millimoles) in water (2 ml), acetonitrile (2 ml) and acetic acid (8 ml) was heated at reflux for 20 h. At this time the mixture was cooled to room temperature and added slowly to 150 ml of cold saturated aqueous NaHCO$_3$. The aqueous layer was extracted with methylene chloride (3×50 ml). The combined extracts were dried over MgSO$_4$ and concentrated in vacuo to an orange oil. Silica gel chromatography using a gradient of 30 to 40% ethyl acetate in hexanes afforded 1 (0.30 g, 0.91 millimole, 68%) as an orange semi-solid: R$_f$=0.22 in 3:2 hexanes: ethyl acetate; IR (KBr pellet) 3353, 1722, 1623, 1525, 1504, 1426, 1342, 1131 cm$^{-1}$; $^1$H-NMR (CDCl$_3$) δ 2.90–3.04 (m, 6H), 3.79 (t,2H,J=6.5 Hz), 7.01 (d,1H,J=9.5 Hz), 8.31 (d,1H,J=9.5 Hz), 8.80 (m,1H), 9.15 (d,1H,J=2.6 Hz) 9.83 (s, 1H); mass spectrum (EI) 331 (M+). Anal. Calcd. for C$_{11}$H$_{13}$N$_3$O$_5$S$_2$: C,39.88; H, 3.93; N, 12.69; S, 19.34. Found: C, 40.01; H, 3.91; N, 12.66; S, 19.34.

(N-2,4-Dinitrophenyl)-2-aminoethyl 3-(1,3-dioxolanyl)-propyl disulfide 7.

This compound was prepared as described above for 6, starting with N,N'-bis-(2,4-dinitrophenyl)-cystamine (2.42 g, 5 millimoles) and 3-(3-mercaptopropyl)-1,3-dioxolane (1.48 g, 10 millimoles), to give 7 (0.60 g, 1.54 millimoles, 15%) as an orange oil: R$_f$=0.43 in 3:2 hexanes: ethyl acetate; IR (thin film) 3360, 2923, 1623, 1592, 1528, 1426, 1335, 1131 cm$^{-1}$; $^1$H-NMR (CDCl$_3$); δ 1.80–1.95 (m,6h), 2.78 (t,2H,J=7.0 Hz), 2.99 (t, 2H,J=6.7 Hz), 3.8–4.0 (m, 6H), 4.87 (t, 1H, J=4.2 Hz), 7.01 (d, 1H, J=9.5 Hz), 8.32 (d, 1H, J=9.5 Hz), 8.79 (s, 1H), 9.16 (d, 1H, J=2.6 Hz); mass spectrum (EI) 389 (M), 368, 359, 294, 279, 256, 225, 210, 196. Anal. Calcd. for C$_{14}$H$_{19}$N$_3$O$_6$S$_2$: C, 43.19; H, 4.88; N, 10.80; S, 16.45. Found: C, 43.27; H, 4.65; N, 10.79; S, 16.40.

(N-2,4-Dinitrophenyl-2-aminoethyl 4-oxobutyl disulfide 2

This compound was prepared as described above for 1, starting with dioxolane 6 (389 mg, 1.0 millimole), to give 2 (340 mg, 0.99 millimole, 99%) as an orange solid: mp 64°–65° C.; R$_f$=0.25 in 3:2 hexanes: ethyl acetate; IR (KBr pellet) 3331, 3092, 2923, 2846, 1722, 1630, 1589, 1525, 1415, 1342, 1247, 1146 cm$^{-1}$; $^1$H-NMR (CDCl$_3$) δ 2.06 (t,2H, J=7.3 Hz), 2.63 (t, 2H, J=7.0 Hz), 2.75 (t, 2H, J=7.1 Hz), 3.00 (t, 2H, J=6.6 Hz), 3.81 (t, 2H,J 6.1 Hz), 7.01 (d, 1H, J=9.5 Hz), 8.31 (d, 1H, J=9.5 Hz), 8.79 (s, 1H), 9.16 (d, 1H, J=2.6 Hz), 9.80 (s, 1H); mass spectrum (EI) 345 (M). Anal. Calcd. for C$_{12}$H$_{15}$N$_3$O$_5$S$_2$: C, 41.74; H, 4.35; N, 12.17; S, 18.55. Found: C, 41.71; H, 4.38; N, 12.11; S, 18.49.

Affinity labels 3, 4, and 5 were prepared as follows:

3-(S-DNP)-mercaptopropanoic acid 8

To a solution of 3-mercaptopropanoic acid (1.59 g, 15 millimoles) in 70 ml of 2.0M aqueous sodium acetate (pH 5.2) was added a solution of 2,4-dinitrofluorobenzene (3.32 g, 18.0 millimoles) in 50 ml of absolute ethanol over 15 min with stirring at room temperature under nitrogen. After 24 hours, the pale yellow solid precipitate was collected and washed with water to give 8 (3.40 g, 12.5 millimoles, 83%): mp 154.5°–157.5° C.; IR (KBr) 3630,3476 (br), 3113, 3082, 1718, 1589, 1511,1344,1055,922 cm$^{-1}$; $^1$H-NMR (acetone-d$_6$) δ 2.71 (t, 2H, J=7.5 Hz), 3.40 (t, 2H, J=7.5 Hz), 3.40 (t, 2H, J=7.4 Hz), 3.40 (s, 1H), 7.87 (d, 1H, J=9.1 Hz), 8.32 (dd, 1H, J=2.5, 9.0 Hz), 8.76 (d, 1H, J=2.5 Hz); mass spectrum (FAB-) 271 (M—H)$^-$, 249, 199, 183, 141, 113, 109. Anal Calcd. for C$_9$H$_8$N$_2$O$_6$S: C, 39.71; H, 2.96; N, 10.29; S, 11.78. Found: C, 39.92; H, 2.96; N, 10.15; S, 11.64.

To a solution of 8 (0.70 g, 2.5 millimoles) in dry dioxane (10 ml) was added thionyl chloride (5 ml). The mixture was stirred under nitrogen for 12 hours. The volatiles were removed in vacuo and the yellow residue was dissolved in dry dioxane (25 ml). A solution of diazomethane (0.6M) in diethyl ether (25 ml) was added. The mixture was stirred at 0° C. for 4 hours after which the volatiles were removed in vacuo. The residue was purified by silica gel chromatography using 9:1 methylene chloride: ethyl acetate as the eluent to give 9 (0.29 g, 0.92 millimoles, 36%) as a yellow solid: mp 117°–119° C.; $R_f=0.52$ in above eluent; IR (KBr pellet) 3458 (br), 3090, 2111, 1637, 1583, 1508, 1340, 1096 cm$^{-1}$; $^1$H-NMR (CDCl$_3$) δ 2.75 (t, 2H, J=7.1 Hz), 3.35 (t, 2H, J=7.3 Hz), 5.32 (s, 1H), 7 61 (d, 1H,J=9.0 Hz), 8.48 (dd, 1H, J=2.5, 9.0 Hz), 9.07 (d, 1H, J=2.5 Hz); mass spectrum (FAB$^-$) 296(M$^-$), 199, 183, 141, 109. Anal. Calcd. for C$_{10}$H$_8$N$_4$O$_5$S: C, 40.54; H, 2.72; N, 18.91; S, 10.82. Found: C, 40.81, H, 2.89; N, 18.59; S, 10.79.

1-Bromo-2-oxo-4-(S-DNP)-mercaptobutane 3

To a solution of 9 (95 mg, 0.32 millimoles) in dry dioxane (5 ml) at 25° C. under nitrogen was added a saturated solution of HBr in dioxane (2 ml). The mixture was stirred for 10 minutes at which time the volatiles were removed completely in vacuo to give pure 3 (130 mg, 0.373 millimoles, 86%) as a yellow solid: mp 99°–101° C.; $R_f=0.78$ in 9:1 methylene chloride: ethyl acetate; IR (KBr) 3106, 3097, 3012, 2958, 1724, 1592, 1510, 1339, 1068, 1053 cm$^{-1}$; $^1$H- NMR (acetone-d$_6$) δ 3.24 (t, 2H, J=7.0 Hz), 3.46 (t, 2H, J=7.0 Hz), 4.28 (s, 2H), 7.98 (d, 1H, J=9.0 Hz), 8.48 (dd, 1H, J =2.5, 9.0 Hz); mass spectrum (FAB$^-$) 268 (M—HBr)$^-$, 233,199,183,109. Anal. Calcd. for C$_{10}$H$_9$BrN$_2$O$_5$S: C, 34.40; H, 2.60; Br,22.89; N, 8.02; S, 9.18. Found C, 34.50; H, 2.60; Br, 22.70; N, 7.88; S, 9.04.

4-(S-DNP)-mercaptobutanoic acid 10

This compound was prepared as described above for 8, starting with 4-mercaptobutanoic acid (1.80 g, 15 millimoles) giving 10 (3.21 g, 11.2 millimoles, 75%) as a pale yellow solid: mp 126.5°–130° C.; IR (KBr) 3528 (br), 3117, 3090, 2948, 1709, 1587, 1518, 1341 cm$^{-1}$; $^1$H-NMR (DMSO-d$_6$) δ 1.85 (m, 2H), 2.34 (t, 2H, J=7.0 Hz), 3.18 (t, 2H, J=7.5 Hz), 3.78 (s, 1H), 7.95 (d, 1H, J=9.1 Hz), 8.41 (dd, 1H, J=2.4, 9.0 Hz), 8.84 (d, 1H, J=2.4 Hz); mass spectrum (FAB$^-$) 285 (M—H)$^-$, 249,199,139. Anal. Calcd. for C$_{10}$H$_{10}$N$_2$O$_6$S: C, 41.96; H, 3.52; N, 9.79; S, 11.20. Found: C, 41.94; H, 3.50; N, 9.60;S, 10.97.

1-Diazo-2-oxo-5-(S-DNP)-mercaptopentane 11

This compound was prepared as described above for 9, starting with 10 (1.00 g, 3.49 millimoles), to give 11 (0.68 g, 2.20 millimoles, 63%) as a yellow solid: mp 84°–86° C.; $R_f=0.52$ in 9:1 methylene chloride:ethyl acetate; IR (KBr) 3106, 2939, 2866, 2104, 1626, 1589, 1513, 1343 cm$^{-1}$; $^1$H-NMR (CDCl$_3$ δ 2.10 (m, 2H), 2.55 (t, 2H, J=5.7 Hz), 3.10 (t, 2H, J=7.5 Hz), 5.29 (s, 1H), 7.74 (d, 1H, J=9.0 Hz), 8.38 (dd, 1H, J=2.5, 9.0 Hz), 9.06 (d, 1H, J=2.4 Hz); mass spectrum (FAB$^-$) 310 (M$^-$), 249, 199, 139, 107. Anal. Calcd. for C$_{11}$H$_{10}$N$_4$O$_5$S: C, 42.58; H, 3.25; N, 18.06; S, 10.33 Found: C, 42.79; H, 3.39; N, 17.93; S, 10.14.

1-Bromo-2-oxo-5-(S-DNP)-mercaptopentane 4.

This compound was prepared as described above for 3, starting with 11 (101 mg, 0.326 millimoles) to give 4 (116 mg, 0.32 millimoles, 98%) as a yellow solid: mp 87°–90° C.; $R_f=0.78$ in 9:1 methylene chloride: ethyl acetate; IR (KBr) 3113, 3009, 2953, 1723, 1592, 1512, 1343 cm$^{-1}$; $^1$H- NMR (DMSO-d$_6$) δ 1.89 (m, 2H), 2.79 (t, 2H, J=7.1 Hz), 3.17 (t, 2H, J=7.4 Hz), 4.36 (s, 2H), 7.88 (d, 1H, J=9.1 Hz), 8.43 (dd, 1H, J=2.5, 9.0 Hz), 8.85 (d, 1H, J=2.6 Hz); Anal. Calcd. for C$_{11}$H$_{11}$BrN$_2$O$_5$S: C, 36.38; H, 3.05; Br, 2.00; N, 7.71. S, 8.83. Found: C, 36.57; H, 3.17; Br, 21,83; N, 7.49; S, 9.01.

5-(S-DNP)-mercaptopentanoic acid 12

This compound was prepared as described above for 8, starting with 4-mercaptopentanoic acid (2.00 g, 15 millimoles) giving 12 (4.20 g, 14.0 millimoles, 93%) as a pale yellow solid: mp 159°–161° C.; IR (KBr) 3117, 2948, (br), 1707, 1587, 1587, 1517, 1341 cm$^{-1}$; $^1$H- NMR (acetone-d$_6$) δ 1.83 (m, 4H), 2.39 (t, 2H, J=6.8 Hz), 2.83 (s, 1H) 3.26 (t, 2H, J=7.0 Hz), 7.95 (d, 1H, J=9.0 Hz), 8.45 (dd, 1H, J=2.5, 9.0 Hz), 8.96 (d, 1H, J=2.5 Hz); mass spectrum (FAB$^-$) 299 (M—H)$^-$, 199,183,141,113,109. Anal. Calcd. for C$_{11}$H$_{12}$N$_2$O$_6$S: C, 44.00; H, 4.03; N, 9.33. S, 10 68. Found: C, 43.83; H, 3.92; N, 9.42; S, 10.59.

1-Diazo-2-oxo-6=(S-DNP)-mercaptohexane 13

This compound was prepared as described above for 9, starting with 12 (1.00 g, 3.33 millimoles), to give 13 (0.70 g, 2.15 millimoles, 65%) as a yellow solid: mp 120°–122° C.; $R_f=0.50$ in 9:1 methylene chloride:ethyl acetate; IR (KBr) 3093, 2937, 2110, 1637, 1584, 1508, 1336, 1109 cm$^{-1}$; $^1$H-NMR (CDCl$_3$) δ 1.83 (m, 4H), 2.39 (t, 2H, J=5.8 Hz), 3.04 (t, 2H, J=7.4 Hz), 5.25 (s, 1H), 7.53 (d, 1H, J=9.0 Hz), 8.37 (dd, 1H, J=2.5, 9.0 Hz), 9.07 (d, 1H, J=2.5 Hz); mass spectrum (FAB$^-$) 324, 307, 267, 199, 183, 141, 109. Anal. Calcd. for C$_{12}$H$_{12}$N$_4$O$_5$S: C, 44.44; H, 3.73; N, 17.28. S, 9.89. Found: C, 44.60; H, 3.74; N, 16.99; S, 9.65.

1-Bromo-2=oxo-6-(S-DNP)-mercaptohexane 5

This compound was prepared as described above for 3, starting with 13 (119 mg, 0.366 millimoles) to give 5 (0.127 g, 0.336 millimoles, 92%) as a yellow solid: mp 80°–83° C.; $R_f=0.78$ in 9:1 methylene chloride: ethyl acetate; IR (KBr) 3121, 2937, 2872, 1719, 1586, 1513, 1339, 1095, 1053; $^1$H-NMR (acetone-d$_6$) δ 1.81 (m, 4H), 2.79 (t, 2H, J=6.6Hz), 3,24 (t, 2H, J=6.8Hz), 4.18 (s, 2H), 7.93 (d, 1H, J=9.0 Hz), 8.45 (dd, 1H, J=2.5, 9.0Hz), 8.95 (d, 1H, J=2.5Hz); mass spectrum (FAB$^-$) 378 (M$^-$),307, 263, 199, 183, 141, 109. Anal. Calcd. for C$_{12}$H$_{13}$BrN$_2$O$_5$S: C,38.21; H,3.47; Br,21.18; N,7.43; S,8.50. Found: C,38.40; H, 3.45; Br,21.34; N,7.34; S,8.46.

Antibody Modification

Affinity Labeling.

The strategy for introducing a thiol into the binding site of MOPC315 is outlined in FIG. 3. These steps were carried out with the Fab fragment, generated by treating the reduced and alkylated IgA with papain followed by affinity chromatography on DNP-coupled Sepharose 4B (Goetzl (1970) Biochemistry 9:1267). The Fab fragment (at 10 μM) was treated with either 1.5 equivalents of aldehydes 1 or 2 for one hour followed by 7.5 equivalents of NaCNBH$_3$, in 0.2M sodium phosphate; pH 7.0, at 37° C. for 20 hours, or with 1.3 equivalents of α-bromoketones 3, 4, or 5 in 0.1M sodium bicarbonate, pH 9.0; at 37° C. for 16 hours. In both cases, the labeled Fab was purified by chromatography on Sephadex G-50 in 0.1M sodium phosphate, pH 7.3, and, after lyophilization, subsequent affinity chromatography on DNP-coupled Sepharose 4B (Goetzl, supra.) to remove unlabeled or non-specifically labeled Fab. The extent of derivatization was quantitated spectrophotometrically (for labels 1 and 2, $\lambda_{max}=360$ nm, , $\epsilon=12,800$ M$^{-1}$ cm$^{-1}$) and additionally, for labels 1 and 2, by incorporation of tritium from NaCNB$^3$H$_3$ (using 12 mCi/millimole NaCNB$^3$H$_3$). With labels 2 and 4, over 90% of the label was incorporated (85% yield after affinity chromatography) (Table 2). In both cases, less than 10% non-specific labeling occurred in the presence of 10 mM of the competitive inhibitor DNP-glycine.

TABLE 2

Incorporation of Affinity Labels into Fab

| compd | % Fab labeled (without DNP-glycine) | % Fab labeled (with DNP-glycine) |
|---|---|---|
| 1 | 22 | 5 |
| 2 | 95 | 10 |
| 3 | 0 | 0 |
| 4 | 85 | 0 |
| 5 | 15 | 0 |

Cleavage of Labels and Isolation of Stable S-Thiopyridyl Adducts.

Cleavage of the Fab affinity-labeled with 2 or 4 (2.0 mg) with 50 mM dithiothreitol in 2 mM EDTA, 0.1M sodium phosphate,pH 8.0 (2 ml) for 12 hours at 37° C. afforded the free thiol The thiol-containing Fab was collected by fast-desalting chromatography using a Pharmacia FPLC column in 0.1M sodium phosphate, pH 7.3, directly into 1.0 ml of a 4.5 mM solution of 2,2'-dithiodipyridine (0.1 sodium phosphate, pH 5.5, containing 15% acetonitrile). This mixture (final volume of 10 ml) was allowed to react at 20° C. for 12 hours after which excess 2,2'-dithiodipyridine was removed by exhaustive dialysis. The thiolated antibody was derivatized in greater than 90% yield (65% recovery in the case of 2) based on the absorbance of thiopyridine at 343 nm ($\epsilon$=7060 m$^{-1}$ cm$^{-1}$) (Grassetti et al. (1967) Arch. Biochem. Biophys. 119:41) after cleavage with 10 mM dithiothreitol, and the protein absorbance at 280 nm (E$_{0.1\%}$=1.37, MW=50,000 for Fab).

Determination of Modified Site

Fab fragments labeled with 2 or 4 were subjected to tryptic digestion and peptide mapping in order to determine the selectivity of thiol incorporation. Fab was affinity-labeled in the presence of label 2 and NaCNB$^3$H$_3$ (12 mCi/millimole) or with $^3$H-labeled 4 (4 mCi/millimole) as described above. $^3$H-labeled 4 was prepared as described for 4, starting with 3,5-$^3$H-2,4-dinitrofluorobenzene. The labeled Fab (1.0 mg/ml) was then denatured in 8M urea, 0.1M Tris-HCl, pH 8.0, reduced with 20 mM dithiothreitol (1 hour at 37° C.) and alkylated with 60 mM Tris-HCl, pH 8.0, reduced with 20 mM dithiothreitol (1 hour at 37° C.) and alkylated with 60 mM iodoacetamide (1 hour at 37° C.). After dialysis against 7 M urea, 20 mM Tris-HCl, pH 8.0, the heavy and light chains were separated by anion exchange chromatography on a Pharmacia Mono Q FPLC column. Separation was achieved at 1.0 ml/min in 7M urea, 20 mM Tris-HCl, pH 8.0, with a linear gradient of 40 mM to 200 mM sodium chloride over 30 min.

In the case of Fab labeled with 2, the heavy chain was found to contain over 95% of the incorporated tritium; with Fab labeled with 4, over 95% of the tritium label was on the light chain. In each case, the radiolabeled chain was dialyzed against 2M urea/100 mM ammonium bicarbonate, pH 8.2, and then treated with trypsin (1:25 w/w trypsin:protein) in the presence of 0.1 mM CaCl$_2$ at 37° C. in the dark. After 8 hours, the reactions were quenched with 10% v/v acetic acid. The radiolabeled peptides were purified by reverse phase HPLC with a 70 min. linear gradient from 0 to 50% acetonitrile in water at 1.0 ml/min; (0.1% and 0.06% (v/v) trifluoroacetic acid was added to the water and acetonitrile, respectively.) Peptides were detected by their absorbance at 214 nm, fractions were collected at 1.0 ml intervals, and aliquots were counted for radioactivity (FIG. 4). Fractions containing radioactivity were rechromatographed using a 70 min. linear gradient from 0 to 50% 2-propanol in water at 0.75 ml/min. The water and the 2-propanol contained 0.1% and 0.06% trifluoroacetic acid, respectively.

The amino acid sequences of the pure peptides were determined on an Applied Biosystems 477A Protein Sequencer. With heavy chain obtained from Fab labeled with 2, all of the detectable derivatization was on leusine 52H. With the light chain from Fab labeled with 4, all of the detectable derivatization was on tyrosine 34L. These residues are identical to those labeled by Givol and co-workers (Haimovich et al. (1972) Biochemistry 11:2389) with the reagents bromoacetyl-N$^\epsilon$-DNP-L-lysine and N-bromoacetyl-N'-DNP-ethylenediamine.

Ester Cleavage Using Thiol-Derivatized Antibody

In addition to modifying the thiolated antibody selectively with catalytic and other groups, the thiol itself can act as a nucleophile in the thiolysis of appropriate substrate. DNP-containing esters 14 and 15 (FIG. 5) were chosen as substrates for the reaction with thiolated Fab labeled with 2 or 4, respectively. The position of the cleavable linkage in affinity label 2 approximates that of the ester in the corresponding substrate 14, ensuring that the thiol is positioned appropriately in the combining site to attack the ester. Likewise, the thiol in Fab labeled with 4 should be positioned to attach ester 15. Moreover, these substrates contain fluorescent coumarin leaving groups, which can readily be detected at nanomolar concentrations.

Synthesis of Substrates (N-DNP)-3-Aminopropanoic acid 7-hydroxycoumarin ester 14.

A mixture of N-DNP-3-aminopropanoic acid (1.28g, 5 millimoles) and 7-hydroxycoumarin (0.81 g, 5 millimoles) in phosphorus oxychloride (8 ml) was heated at reflux under nitrogen for 2 hours. The mixture was cooled to room temperature and added to 60 ml of cold water. The brown solid was filtered, washed with cold water and dried in vacuo. Trituration with acetone gave 14 (0.79 g, 2.0 millimoles, 40%) as a light brown solid; mp 155°-156° C., IR (KBr pellet) 3374, 3107, 2368, 1750, 1722, 1624, 1532, 1426, 1349, 1159, 1127 cm$^{-1}$; $^1$H NMR (DMSO-d$_6$) δ 3.04 (t, 2H, J=6.7Hz), 3.90 (t, 2H, J=6.5Hz), 6.48 (d, 1H, J=9.6 Hz), 7.17 (d, 1H, J=8.4Hz), 7.30 (s, 1H), 7.37 (d, 1H, J=9.7Hz), 7.78 (d, 1H, J=8.5Hz), 8.07 (d, 1H, J=9.3Hz), 8.29 (d, 1H, J=9.6Hz), 8.87 (s, 1H), 8.99 (m, 1H); mass spectrum (FAB+) 400(MH+). Anal. Calcd. for C$_{18}$H$_{13}$N$_3$O$_8$: C, 54.14; H, 3.26; N, 10.53. Found: C, 54.05; H, 3.26; N, 10.23.

2,4-Dinitrobenzoic acid, 7-hydroxycoumarin ester 15

A mixture of 2,4-dinitrobenzoic acid (1.06 g, 5.0 millimoles) and 7-hydroxycoumarin (0.81 g, 5.0 millimoles) in phosphorus oxychloride (4 ml) was heated at reflux with a calcium sulfate drying tube for 40 min. The mixture was cooled to room temperature and added to water (40 ml). The brown solid was filtered, washed with cold water and dried in vacuo to give 15 (1.32 g, 3.7 millimoles, 74%) as a red-brown solid: mp 200°-205° C.; IR (KBr) 3107, 3057, 2364, 1736, 1619, 1544, 1348, 1246, 1122 cm$^{-1}$; $^1$H-NMR (DMSO-d$_6$) δ 6.53 (d, 1H, J=9.6 Hz), 7.34 (dd, 1H, J=2.2, 8.5Hz), 7.47 (d, 1H, J=2.1 Hz), 7.89 (d, 1H, J=8.5Hz), 8.12 (d, 1H, J=9.6Hz), 8.44 (d, 1H, J=8.4Hz), 8.78 (dd, 1H, J=2.2, 8.4Hz), 8.93 (d, 1H, J=2.2Hz); mass spectrum (EI) 356 (M$^+$,) 195, 162, 134, 122. Anal. Calcd. for $C_{16}H_8N_2O_8$: C, 53.94; H, 2.26; N, 7.86. Found: C, 52.18; H, 2.29; N, 7.51.

Ester Cleavage Assays

Cleavage of DNP coumarin esters 14 and 15 by the thiol-containing antibodies was assayed in the presence and absence of 0.1 μM NaCl, 50 mM sodium phosphate, pH 7.0, with 24 μM dithiothreitol at 10° C. The release of free coumarin was quantitated fluorometrically, exciting at 355 nm and measuring emission at 455 nm. The S-thiopyridyl Fab was first dialyzed against assay buffer, 30 min. prior to the assays, an aliquot of the thiopyridyl Fab (0.15 mg in 0.19 ml) was reduced with 3.8 mM dithiothreitol at 20° C. For each assay, reduced, thiolated Fab (15 μg in 18.8 μl) was diluted with assay buffer (2.95 ml) so that the net concentrations of thiolated Fab and of dithiothreitol were 0.1 μM and 24 μM, respectively. After equilibrating, the substrate was added (30 μl of a stock solution in acetonitrile) and the solution mixed for 10 sec. before monitoring fluorescence change. Antibody rates were corrected by subtracting the rate of cleavage in the absence of Fab.

The antibody affinity-labeled with 2 was found to accelerate the cleavage of ester 14 by a factor of 6×10$^4$ over the cleavage reaction in equimolar dithiothreitol. The reaction kinetics are consistent with the formation of a Michaelis complex (FIG. 6). The kinetic constants $k_{cat}$ and $K_m$ for the reaction are 0.87 min$^{-1}$ and 1.2 μM, respectively. The thiolysis reaction was competitively inhibited

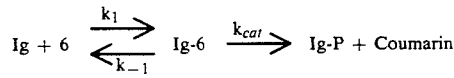

by DNP-glycine with a $K_i$ of 8 μM. Neither the uncleaved affinity-labeled antibody nor the iodoacetamide-alkylated antibody accelerated the rate of the thiolysis reaction above the background rate. The stoichiometry of product release corresponded to 1.0 coumarin to 1.0 Fab-SH. Addition of hydroxylamine to the reaction buffer did not lead to multiple turnovers. However, The introduction of both a thiol and a general base into the label may lead to a catalytic system (Bruice (1959) J. Am. Chem. Soc. 81:5444 and Street et al. (1985) J. Am. Chem.Soc. 107:7669). Interestingly, thiolated Fab labeled with bromoketone 4 did not hydrolyze esters 6, 7, or DNP-acetate. Fluoroescence quenching experiments revealed that the derivatization Fab did not bind the substrate with appreciable affinity, presumably as a result of steric congestion of the antibody combining site (FIG. 7).

Derivatization with a Spectroscopic Probe

In order to demonstrate that the thiolated Fab can be further derivatized with a reporter molecule, N-fluoresceinthioureido-2-mercaptoethylamine (Zackerman et al. (1987) Nucleic Acids Res. 15:5305) was selectively introduced via a disulfide exchange reaction (FIG. 3). The S-thiopyridyl Fab labeled with 2 (9.0 nanomoles in 0.50 ml of 0.1M sodium phosphate, pH 7.3) was treated with N-fluoresceinthioureido-2-mercaptoethylamine (52 nanomoles in 0.50 of 0.1M triethylammonium acetate, pH 7.5, containing 10% acetonitrile) at 23° C. The reaction was monitored by release of thiopyridore at 343 nm (Grassetti and Murray (1967) Arch. Biochem. Biophys. 119:41). After three hours, no additional thiopyridone was released and the mixture was dialyzed exhaustively against assay buffer (50 mM NaCl, 50 mM sodium phosphate, pH 7.0). The resulting adduct was isolated in 84% overall yield, with greater than 90% incorporation of the fluorophore.

Fluorescence Quenching Binding Assay.

Addition of the ligand DNP-glycine to the fluorescein-Fab adduct resulted in a decrease in fluorescence, providing a direct assay of ligand binding (FIG. 7). Fluorescence quenching experiments were carried out at 10° C. using 492 nm for excitation and measuring emission at 521 nm. The fluorescein-Fab adduct was diluted with assay buffer (50 mM NaCl. 50 mM sodium phosphate, pH 7.0) to 0.10 μM. Aliquots of 2,4-DNP-glycine were added and, after mixing, the fluorescence observed. The association constant of DNP-glycine to the fluorescein-Fab adduct was determined to be 3.0×10$^5$ M$^{-1}$, almost identical to the $K_A$ of DNP-glycine to underivatized MOPC 315, 2.0×10$^5$ M$^{-1}$. Addition of DNP-glycine to a solution of one equivalent free N-fluoresceinthioureido-2-mercaptoethylamine and underivatized Fab (each at 0.10 μM) resulted in no detectable fluorescence change (FIG. 7).

Although the foregoing invention has been described in some detail by way of illustration and example for purposes of clarity of understanding, it will be obvious that certain changes and modifications may be practiced within the scope of the appended claims.

What is claimed is:

1. A method for introducing an active functionality to a polypeptide proximate a binding site, said method comprising:
    combining the polypeptide with a ligand capable of binding to the binding site, said ligand having a first reactive group cleavably attached thereto;
    covalently attaching the first reactive group to an amino acid side chain on the polypeptide, wherein said amino acid side chain is at a distance less than 10 Å from the binding site and at a location where the active functionality does not substantially interfere with binding of a target ligand to the binding site;
    cleaving the first reactive group from the ligand, whereby a moiety of the reactive group remains bound to the polypeptide through the amino acid side chain; and
    removing the ligand from the polypeptide.

2. A method as in claim 1, wherein the remaining moiety is the active functionality and is selected from the group consisting of catalytic functionalities and reactive functionalities.

3. A method as in claim 1, wherein the moiety is a thiol.

4. A method as in claim 1, wherein cleavage of the reactive group provides a moiety which is selected from the group consisting of thiol, aldehyde, and aromatic amine.

5. A method as in claim 4, further comprising covalently attaching a second functionality to the remaining moiety of the first reactive group, wherein the second functionality is the active functionality selected from the group consisting of catalytic functionalities, reactive functionalities, labeling groups, and chemotherapeutic agents.

6. A method as in claim 2 or 5, wherein the active functionality is a catalytic functionality selected from the group consisting of acids, bases, enzyme cofactors, metal complexes, photoactive molecules, nucleophiles, electrophiles, and redox active molecules.

7. A method as in claim 2 or 5, wherein the active functionality is a reactive functionality selected from the group consisting of alkylating agents, oxidizing agents, reducing agents, hydrolytic agents, and photoactive agents.

8. A method as in claim 5, wherein the active functionality s a detectable label selected from the group consisting of fluorophores, chemiluminescers, bioluminescers, dyes, spin labels, flavins, piezoelectric molecules and biotin.

9. A method as in claim 5, wherein the active functionality is a chemotherapeutic agent selected from the group consisting of toxins, toxin fragments, bactericides, radical scavengers, radical generators, alkylating agents, neurotransmitters, radionuclides, antiviral compounds, antifungal compounds, antineoplastic agents, antimycoplasmal agents, and heavy metals.

10. A method as in claim 1, wherein the polypeptide is selected from the group consisting of antibodies, antibody fragments, enzymes, enzyme fragments, hormones, lymphokines, lectins, avidin, proteins of the MHC, T-cell receptors, G proteins, neurotransmitter receptors, and DNA binding proteins.

11. A method for introducing a reactive group to a location proximate a binding site on an antibody molecule selected from the group consisting of antibodies and antibody fragments, said method comprising:
   combining the antibody or antibody fragment with a ligand capable of binding to the binding site, said ligand having a first reactive group cleavably attached thereto;
   covalently attaching the first reactive group to an amino acid side chain on the antibody molecule, wherein said amino acid side chain is at a distance less than 5 Å from the binding site and at a location where the reactive group does not substantially interfere with binding of a target ligand to the binding site;
   cleaving the first reactive group from the ligand whereby a moiety of the reactive group remains bound to the antibody molecule through the amino acid side chain; and
   removing the ligand from the antibody molecule.

12. A method as in claim 11, wherein the remaining moiety is the active functionality and is selected from the group consisting of catalytic functionalities and reactive functionalities.

13. A method as in claim 11, wherein the remaining is a thiol.

14. A method as in claim 11, wherein cleavage of the reactive group provides a moiety which is selected from the group consisting of diazoketones, aromatic azides, diazonium, thiol, α-bromoketone, epoxide, and aldehyde.

15. A method as in claim 14, further comprising covalently attaching a second functionality to the remaining moiety of the first reactive group, wherein the second functionality is the active functionality selected from the group consisting of catalytic functionalities, reactive functionalities, labeling groups, and chemotherapeutic agents.

16. A method as in claims 12 or 15, wherein the active functionality is a catalytic functionality selected from the group consisting of acids, bases, enzyme cofactors, metal complexes, photoactive molecules, nucleophiles, electrophiles, and redox active molecules.

17. A method as in claim 12 or 15, wherein the active functionality is a reactive functionality selected from the group consisting of alkylating agents, oxidizing agents, reducing agents, hydrolytic agents, and photoactive agents.

18. A method as in claim 15, wherein the active functionality is a detectable label selected from the group consisting of fluorophores, chemiluminescers, bioluminescers, dyes, spin labels, flavins, piezoelectric molecules and biotin.

19. A method as in claim 15, wherein the active functionality is a chemotherapeutic agent selected from the group consisting of toxins, toxin fragments, bactericides, radical scavengers, radical generators, alkylating agents, neurotransmitters, radionuclides, antiviral compounds, antifungal compounds, antineoplastic agents, antimycoplasmal agents, and heavy metals.

20. A method as in claim 11, wherein the antibody molecule is an antibody raised against a target ligand.

21. A method as in claim 20, wherein the ligand having the cleavably attached reactive group is the target ligand.

* * * * *